US006252041B1

(12) United States Patent
Yanai et al.

(10) Patent No.: US 6,252,041 B1
(45) Date of Patent: Jun. 26, 2001

(54) DEPSIPEPTIDES CONTAINING NON-NATURAL AMINO ACIDS

(75) Inventors: Makoto Yanai; Masashi Suzuki; Norio Oshida; Koji Kawamura; Shigeru Hiramoto; Orie Yasuda; Nobuhiro Kinoshita; Akiko Shingai; Masako Takasu, all of Saitama-ken (JP)

(73) Assignee: Nisshin Flour Milling Co., Ltd., Tokyo (JP)

( * ) Notice: Subject to any disclaimer, the term of this patent is extended or adjusted under 35 U.S.C. 154(b) by 0 days.

(21) Appl. No.: 09/235,479

(22) Filed: Jan. 22, 1999

(30) Foreign Application Priority Data

Jan. 27, 1998 (JP) .................................... 10-014037

(51) Int. Cl.[7] .................................... C07K 5/08
(52) U.S. Cl. .................... 530/331; 530/330; 530/332; 514/17; 514/18; 514/19
(58) Field of Search .............. 514/19, 18, 17; 530/330, 331, 332

(56) References Cited

U.S. PATENT DOCUMENTS 5,801,143   9/1998  Hiramoto et al. .............. 514/9

FOREIGN PATENT DOCUMENTS 0 761 682   3/1997  (EP) .

OTHER PUBLICATIONS

Abstract of WO 97/49722, Dec. 31, 1997.*
Derwent Abstract of WO 97/49724, Dec. 31, 1997.*
Michael J. Ignatius, et al., "Expression of Apolipoprotein E During Nerve Degeneration and Regeneration", Proc. Natl. Acad. Sci. USA, Neurobiology, vol. 83, Feb. 1986, pp. 1125–1129.
Nobuhiro Yamada, et al., "Increased Clearance of Plasma Cholesterol After Injection of Apolipoprotein E Into Watanabe Heritable Hyperlipidemic Rabbits", Proc. Natl. Acad. Sci. USA, Medical Sciences, vol. 86, Jan. 1989, pp. 665–669.
Hitoshi Shimano, et al., "Plasma Lipoprotein Metabolism in Transgenic Mice Overexpressing Apolipoprotein E",Journal of Clinical Investigation, vol. 90, Nov. 1992, pp. 2084–2091.
Masao Shiozaki, et al., Tetrahedron Letters, vol. 37, No. 22, pp. 3875–3876, May 1996.
Takeshi Oshima, et al., Peptide Chemistry, 29TH Symposium on Peptide Chemistry, 1995.

* cited by examiner

*Primary Examiner*—Christopher S. F. Low
*Assistant Examiner*—David Lukton
(74) *Attorney, Agent, or Firm*—Oblon, Spivak, McClelland, Maier & Neustadt, P.C.

(57) ABSTRACT

A depsipeptide containing a non-natural amino acid(s) having the formula (1)

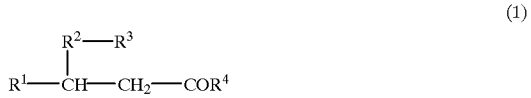

(1)

wherein $R^1$ represents a $C_5$–$C_{20}$ alkyl group and others; $R^2$ represents —O—CO—CH($R^5$)—X—CH($R^6$)—NH— (wherein X represents N($R^7$)—CO, $CH_2$—CO, $CH_2$—$CH_2$ and others, $R^5$, $R^6$, and $R^7$ represent a hydrogen atom or a $C_1$–$C_6$ alkyl group); $R^3$ represents

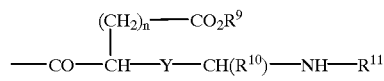

and wherein the remaining substituent variables are as defined herein.

The above depsipeptides have a promoting activity on the production of apolipoprotein E, and are useful as a therapeutic agent for neurologic damages, especially dementia, and hyperlipemia.

16 Claims, No Drawings

DEPSIPEPTIDES CONTAINING NON-NATURAL AMINO ACIDS

BACKGROUND OF THE INVENTION

1. Field of the Invention

This invention relates to a novel depsipeptide and a pharmaceutical composition containing the same as an active ingredient. The depsipeptides of the invention have a promoting activity on the production of apolipoprotein E and are useful as therapeutic agents for neurologic damages, especially dementia, and hyperlipemia.

2. Description of the Prior Art

As a therapeutic agent for senile dementia, there have been mainly applied activators of cerebral circulation and metabolism, but these drugs have no improving effect on disintegration of the central nervous system which is believed to cause senile dementia. Consequently, they could not show any improving effect on dysmnesia or acaculia which is said to be the main symptom of dementia. In view of this, there has been desired as a new type of the therapeutic agent for senile dementia a drug which may promote repair and growth of nervous systems while inhibiting the disintegration of the central nervous system.

On the other hand, it has been reported that apolipoprotein E may be generated at a high level at the damaged sites of nervous systems which are being repaired (For example, refer to M. J. Igunatius et al., Proc. Natl. Acad. Sci. U.S.A., 83, 1125 (1986)), which suggests that apolipoprotein E will play an important role in repairing the damaged nervous systems. Moreover, it has recently been reported that a remarkable reduction in a plasma cholesterol level is observed when apolipoprotein E is administered intravenously to WHHL rabbit which is a model animal for human familial hypercholesterolemia homozygote (Yamada et al., Proceeding of National Academy Science USA, Vol. 86, pp. 665–669, 1989). Also, it has been reported that plasma cholesterol and plasma triglyceride can be noticeably decreased by transducing a gene for apolipoprotein E into the mouse liver and expressing apolipoprotein E in a large mass (Shimano, H. et al., Journal of Clinical Investigation, Vol. 90, pp. 2084–2091, 1992).

As is apparent from these reports, an increase in apolipoprotein E level in plasma has been regarded as extremely effective for the treatment of hyperlipemia, especially, familial hypercholesterolemia homozygote which has been hitherto considered as difficult to be treated with the prior art drugs.

DETAILED DESCRIPTION OF THE INVENTION

Under these circumstances, the present inventors have made earnest studies to provide a drug for promoting the production of apolipoprotein E, and as a result, the depsipeptide derivatives having a specific structure may possess such activities, upon which the invention has been completed.

The present invention relates to a depsipeptide having the formula (1):

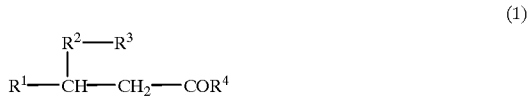

wherein
$R^1$ represents a straight or branched $C_5$–$C_{20}$ alkyl group or a straight or branched $C_5$–$C_{15}$ alkoxymethyl group,
$R^2$ represents

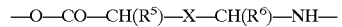

(wherein X represents $N(R^7)$—CO, $N(R^8)$—$CH_2$, $CH_2$—CO, $CH_2$—$CH_2$, CH=CH, $CH_2$—CH(OH) or CH(OH)—CH(OH), $R^5$, $R^6$, $R^7$ and $R^8$ represent a hydrogen atom or a straight or branched $C_1$–$C_6$ alkyl group),
$R^3$ represents

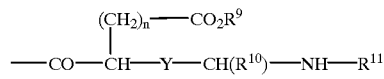

(wherein Y represents $N(R^{12})$—CO, $N(R^{13})$—$CH_2$, $CH_2$—CO, $CH_2$—$CH_2$, CH=CH, $CH_2$—CH(OH) or CH(OH)—CH(OH), n represents an integer of 1–3, $R^9$, $R^{10}$, $R^{12}$ and $R^{13}$ represent a hydrogen atom or a straight or branched $C_1$-$C_6$ alkyl group and $R^{11}$ represents a protecting group for an amine commonly used in peptide chemistry),
$R^4$ represents a hydroxyl group, a straight or branched $C_1$–$C_6$ alkoxy group, a benzyloxy group, A, A-B or

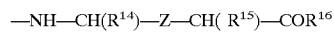

(wherein Z represents $CH_2$—$N(R^{17})$, CO—$CH_2$, CO—$N(R^{18})$, $CH_2$—$CH_2$, CH=CH, CH(OH)—$CH_2$ or CH(OH)—CH(OH), $R^{14}$ represents a hydrogen atom, a straight or branched $C_1$–$C_6$ alkyl group or —$(CH_2)_m$—$COR^{19}$, $R^{15}$, $R^{17}$ and $R^{18}$ represent a hydrogen atom or a straight or branched $C_1$-$C_6$ alkyl group, $R^{16}$ represents a hydroxyl group, a straight or branched $C_1$–$C_6$ alkoxy group or a benzyloxy group, $R^{19}$ represents a hydroxyl group, an amino group or a $C_1$–$C_6$ alkoxy group, and m represents an integer of 1–3),
A represents a residue of an amino acid selected from the group of alanine, valine, leucine, isoleucine, phenylalanine, tyrosine, proline, aspartic acid, asparagine, glutamic acid, glutamine, serine, lysine and β-t-butylalanine or an N-methyl derivative of said amino acid residue,
B represents a residue of an amino acid selected from the group of alanine, valine, leucine, isoleucine, serine, threonine, lysine, hydroxylysine, arginine, cysteine, methionine, phenylalanine, tyrosine, tryptophan, histidine, proline, 4-hydroxyproline, aspartic acid, asparagine, glutamic acid, glutamine, piperidine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl)

piperidylalanine, 3-(2-naphthyl)alanine, β-cyclohexylalanine, β-t-butylalanine, 9-anthracenylalanine, α-methylalanine and 2-aminobutanoic acid or an N-methyl derivative of said amino acid residue, when the amino acid for A or B contains a free amino group, free carboxyl group, free ω-carbamido group, free hydroxyl group, free mercapto group and/or an N-terminal amino group, said free group may be protected by a group commonly used in peptide chemistry, respectively, and when A and B are lysine, hydroxylysine, glutamic acid or aspartic acid, either α- or ω-amino or carboxyl group existing in said residue may form a peptide linkage with its adjacent amino acid;

except that X is $N(R^7)$—CO, Y is $N(R^{12})$—CO and $R^4$ is hydroxyl, straight or branched alkoxy having 1–6 carbon atoms, benzyloxy, A, A—B or —NH—CH$(R^{14})$—Z—CH$(R^{15})$—COR$^{16}$ (wherein Z is CO—N$(R^{18})$);

or a pharmacologically acceptable salt thereof.

The invention also relates to a pharmaceutical composition which comprises as an active ingredient a depsipeptide containing non-natural amino acids as described above or a pharmacologically acceptable salt thereof.

Specifically, the invention relates to a pharmaceutical composition for promoting the production of apolipoprotein E which comprises as an active ingredient a depsipeptide containing non-natural amino acids as described above or a pharmacologically acceptable salt thereof.

Further, the invention relates to a pharmaceutical composition for treating neurologic damages, dementia or hyperlipemia which comprises as an active ingredient a depsipeptide containing non-natural amino acids as described above or a pharmacologically acceptable salt thereof.

Further, the invention relates to a method for treating neurologic damages, dementia or hyperlipemia which comprises administering a therapeutically effective amount of a depsipeptide containing non-natural amino acids as described above or a pharmacologically acceptable salt thereof to a host affected with neurologic damages, dementia or hyperlipemia.

Furthermore, the invention also relates to use of the depsipeptide containing non-natural amino acids as described above or a pharmacologically acceptable salt thereof for treating neurologic damages, dementia or hyperlipemia.

In the formula (1), there may be preferably mentioned that X is CH=CH or $CH_2$—$CH_2$, Y is $N(R^{12})$—CO or $N(R^{13})$—$CH_2$ and $R^4$ is a hydroxyl group, A, A—B or —NH—CH$(R^{14})$—Z—COR$^{15})$—COR$^{16}$ (wherein Z is CH=CH).

Preferable compounds of the formula (1) include the compounds wherein X is CH=CH, Y is $N(R^{12})$—CO or $N(R^{13})$—$CH_2$ and $R^4$ is a hydroxyl group, A, A—B or —NH—CH$(R^{14})$—Z—CH$(R^{15})$—COR$^{16}$ (wherein Z is CH=CH).

There may be preferably mentioned the depsipeptides containing non-natural amino acids of the above formula (1) wherein $R^4$ is a hydroxyl group or A is aspartic acid, asparagine, glutamic acid or glutamine, B is alanine, valine, leucine, isoleucine, phenylalanine, tyrosine, proline, aspartic acid, asparagine, glutamic acid, glutamine or β-t-butylalanine, or a pharmacologically acceptable salt thereof.

In the above formula (1), $R^{16}$ is preferably a hydroxyl group.

The above amino acids which the non-natural amino acid-containing depsipeptide of the invention is composed of may be in the form of either L-isomer or D-isomer, while in A or B in the formula (1), the free amino group, free carboxyl group, free ω-carbamido group, free hydroxyl group, free mercapto group and/or an N-terminal amino group may be protected by a group commonly used in peptide chemistry, respectively, and when A and B are lysine, hydroxylysine, glutamic acid or aspartic acid, either α- or ω- amino or carboxyl group existing in said residue may form a peptide linkage with its adjacent amino acid.

As the protecting groups which may be applied for protecting a free amino group in the amino acid residue, there may be mentioned, for example, a t-butoxycarbonyl (hereinafter referred to as "Boc") group, a benzyloxycarbonyl group (hereinafter referred to as "Cbz"), a p-methoxybenzyloxycarbonyl group or a 9-fluorenylmethoxycarbonyl group (hereinafter referred to as "Fmoc") or the like; a benzyloxy group (hereinafter referred to as "OBzl") or a t-butoxy group (hereinafter referred to as "OtBu"), a phenacyloxy group (hereinafter referred to as "OPac") or the like as a protecting group for a free carboxyl group; 4,4'-dimethoxybenzhydryl (hereinafter referred to as "Mbh") group, a trityl group (hereinafter referred to as "Trt") or the like as a protecting group for ω-carbamido group of Gln or Asn; an OBzl group, an OtBu group or the like as the protecting group for a free hydroxyl group; a benzyl group, a Trt group, an acetamidomethyl group or the like as the protecting group for a free mercapto group in the amino acid residue.

As the protecting group for an N-terminal amino group in the above depsipeptide, there may be mentioned those protecting groups commonly used in peptide chemistry such as a Boc group, a Cbz group, a p-methoxybenzyloxycarbonyl group, a Fmoc group or the like.

As the protecting group for a C-terminal carboxyl group in the above depsipeptide, there may be mentioned an OBzl group, an OtBu group, an OPac group or the like.

The depsipeptides of the above formula (1) according to the invention have a promoting activity on the production of apolipoprotein E in Hep G2 cells having various functions in the liver. Since apolipoprotein E has a repairing action on neurologic damages and further a lowering action on cholesterol and triglyceride levels in the blood, the depsipeptides of the invention which promote the production of apolipoprotein E are useful as therapeutic agents for neurologic damages, especially dementia, and hyperlipemia.

The depsipeptides containing non-natural amino acids and having the above formula (1) according to the invention or pharmacologically acceptable salts thereof may be prepared according to any methods conventionally employed for peptide synthesis. For example, there may be employed a condensing agent method, an azide method, a chloride method, an acid anhydride method, a mixed anhydride method, an active ester method, a redox method, an enzyme method or the like as disclosed in Nobuo Izumiya et al., "Fundamentals and Experiments for Peptide Synthesis (in Japanese)", issued from Maruzen Co., Ltd., 1985.

The depsipeptides containing non-natural amino acids of the invention or pharmacologically acceptable salts thereof may be prepared, for example, by protecting or activating the carboxyl group of a 3-hydroxycarboxylic acid represented by the formula (2)

(2)

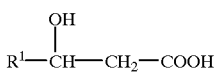

(wherein $R^1$ is as defined above) and then condensing the hydroxyl group of the 3-hydroxycarboxylic acid with the carboxyl group of an aminocarboxylic acid having the protected N-terminal group as required and having the formula

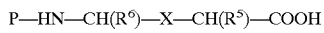

P—HN—CH(R⁶)—X—CH(R⁵)—COOH (wherein P represents a protecting group for an amino group) and the carboxyl group of the 3-hydroxycarboxylic acid with the amino group of an aminocarboxylic derivative as required and having the formula

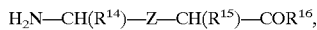

H₂N—CH(R¹⁴)—Z—CH(R¹⁵)—COR¹⁶, respectively, according to a conventional method, leaving the protecting group at the N-terminal or C-terminal and subsequently condensing the amino group and carboxyl group in turn with desired amino acids according to a conventional method for peptide synthesis.

Alternatively, the depsipeptides may be prepared by previously condensing the above aminocarboxylic acid with necessary amino acids followed by binding with the hydroxyl group or carboxyl group of the above hydroxycarboxylic acid via an ester bond or an amide bond.

The protection of the carboxyl group in the compound of the above formula (2) may be carried out according to the esterification reaction for methyl esters by reacting with diazomethane in a solvent of ether, methanol or the like under ice-cooling or at room temperature or the esterification reaction for benzyl esters by reacting with benzyl bromide in the presence of a basic substance such as triethylamine in a solvent such as dimethylformamide (hereinafter referred to as "DMF"), dimethyl sulfoxide (hereinafter referred to as "DMSO") or the like at a temperature of from room temperature to heating temperature.

The condensation of an amino acid to the hydroxyl group in a compound having the protected carboxyl group may be carried out by employing a condensing reagent N,N'-dicyclohexylcarbodiimide (hereinafter referred to as "DCC") or 1-ethyl-3-(3'-dimethylaminopropyl) carbodiimide hydrochloride, i.e. water-soluble carbodiimide (hereinafter referred to as "WSCI") or the like in a solvent such as ether, acetone, chloroform, dichloromethane, ethyl acetate, DMF, tetrahydrofuran (hereinafter referred to as "THF"), acetonitrile, DMSO or the like under ice-cooling or at room temperature, preferably in the presence of an acylation catalyst such as dimethylaminopyridine (hereinafter referred to as "DMAP") or the like.

As the 3-hydroxycarboxylic acid of the formula (2) which is a starting material for the depsipeptide of the invention, there may be illustratively mentioned 3-hydroxycaprylic acid, 3-hydroxypelargonic acid, 3-hydroxycapric acid, 3-hydroxylauric acid, 3-hydroxymyristic acid, 3-hydroxypalmitic acid, 3-hydroxymargaric acid, 3-hydroxystearic acid, 4-octyloxy-3-hydroxybutyric acid, 4-nonyloxy-3-hydroxybutyric acid, 4-decyloxy-3-hydroxybutyric acid, 4-undecyloxy-3-hydroxybutyric acid, 4-dodecyloxy-3-hydroxybutyric acid, 4-tridecyloxy-3-hydroxybutyric acid or the like.

Such 3-hydroxycarboxylic acid of the formula (2) may be employed in the form of an optically active isomer, R- or S-isomer or a racemate thereof. When $R^1$ is a straight or branched $C_5$–$C_{20}$ alkyl group, the R-isomer may be preferably used, while when $R^1$ is a straight or branched $C_5$–$C_{15}$ alkoxymethyl group, the S-isomer may be preferably used.

In preparing the depsipeptide of the invention, when a condensing agent is to be used, there may be used DCC, WSCI, O-(1H-benzotriazol-1-yl)-N,N,N',N'-tetramethyluronium tetrafluoroborate (TBTU), benzotriazol-1-yl-oxy-tris(dimethylamino)phosphonium hexafluorophosphate (BOP), O-(7-azabenzotriazol-1-yl)-1,2,3-tetramethyluronium hexafluorophosphate (HATU) and the like. It is also preferable to simultaneously add an additive commonly employed for preventing racemization such as N-hydroxysuccinimide, N-hydroxybenzotriazole (hereinafter referred to as "HOBt"), N-hydroxy-5-norbornene-2,3-dicarbodiimide, 1-hydroxy-7-azabenzotriazole (HOAt) and the like.

When the azide method is applied, there may be employed diphenyl-phosphoric acid azide (hereinafter referred to as "DPPA") and the like as a main condensing agent.

Any protecting procedure is preferably applied to the carboxyl group, amino group, ω-carbamido group and the like which would not participate in the said condensation reaction, according to any conventional and well-known procedures, before carrying out the condensation reaction.

In this case, various protecting groups as mentioned above may be applied for the said protecting procedure.

Removal of the protecting group in the steps for the preparation of the depsipeptide of the invention is required to leave the protecting group without giving any influence upon the peptide linkage, and may be appropriately selected in compliance with the type of the protecting group used.

The solvents which may be employed for the respective peptide syntheses as described above are, for example, chloroform, dichloromethane, ethyl acetate, DMF, DMSO, pyridine, dioxane, THF, dimethoxyethane, acetonitrile, etc. and any combination of two or more thereof may be used, if necessary. Also, this condensation reaction is carried out at a temperature ranging about −20° C. to 50° C. similarly to conventional condensation reactions.

For the present synthesis, there may be used any of a liquid phase method and a solid phase method, while a column method or a batch method may be also applicable herein.

The depsipeptides of the invention in the form of salts thereof may be converted to the corresponding free form, and the so-obtained depsipeptides of the invention in the form of the free form thereof may be converted to the corresponding pharmacologically acceptable salts thereof. In the latter case, when the depsipeptide is in the form of an acidic compound due to the carboxyl group involved therein, there may be formed salts with inorganic bases such as sodium, potassium, calcium and ammonium salts or the like and with organic bases such as triethylamine salt, and when the depsipeptide is in the form of a basic compound due to the amino group involved therein, there may be formed salts with inorganic acids such as hydrochloric acid, hydrobromic acid, sulfuric acid and phosphoric acid or the like and with organic acids such as acetic acid, succinic acid, oxalic acid, malic acid, tartaric acid or the like.

The depsipeptides or pharmacologically acceptable salts thereof according to the invention may be formulated to pharmaceutical preparations of various dosage forms. More specifically, such pharmaceutical preparations may be, for example, solid preparations such as tablets, hard capsules, soft capsules, granules, powders, etc. and liquid preparations such as solutions, emulsions, suspensions, etc. As the preparations for parenteral administration may be mentioned injections, suppositories, etc.

In preparing such pharmaceutical preparations, they may be formulated by incorporating additives conventionally used for preparing such pharmaceutical preparations, for example, excipients, stabilizers, antiseptics, solubilizing agents, wetting agents, emulsifying agents, lubricants, sweetening agents, coloring agents, flavoring agents, isotonic agents, buffering agents, antioxidants and the like.

As the additives, there may be mentioned, for example, starch, sucrose, fructose, lactose, glucose, mannitol, sorbitol, precipitated calcium carbonate, crystalline cellulose, carboxymethylcellulose, dextrin, gelatin, acacia, magnesium stearate, talc, hydroxypropylmethylcellulose and the like.

Where the depsipeptide of the invention is to be applied in the form of solutions or injections, the depsipeptide of the invention may be used by dissolving or suspending in any conventional diluent. The diluent may include, for example, physiological saline, Ringer's solution, an aqueous glucose solution, an alcohol, a fatty acid ester, glycerol, a glycol, an oil derived from plant or animal sources, a paraffin and the like.

These preparations may be prepared according to a conventional method.

A usual clinical dose may be in the range of 0.5–2000 mg per day for adult when orally given, more preferably, in the range of 1–1000 mg, and more preferably in the range of 5–500 mg.

A daily dose for adult via parenteral administration may be used in the range of 0.05–5000 mg.

The production of the bicyclic depsipeptide of the invention will be illustrated below by way of Examples, and the test for the productivity of apolipoprotein E by the depsipeptide of this invention will be explained by way of Test Examples and the pharmaceutical containing as an active ingredient the depsipeptide of this invention will be explained by way of Preparation Examples.

The following Reaction Schemes 1 to 6 correspondingly illustrate the reaction steps in Examples 1 to 6, respectively. Accordingly, Compound Nos. and Intermediate Nos. in the Reaction Schemes correspond to those in Examples.

Reaction Scheme 1

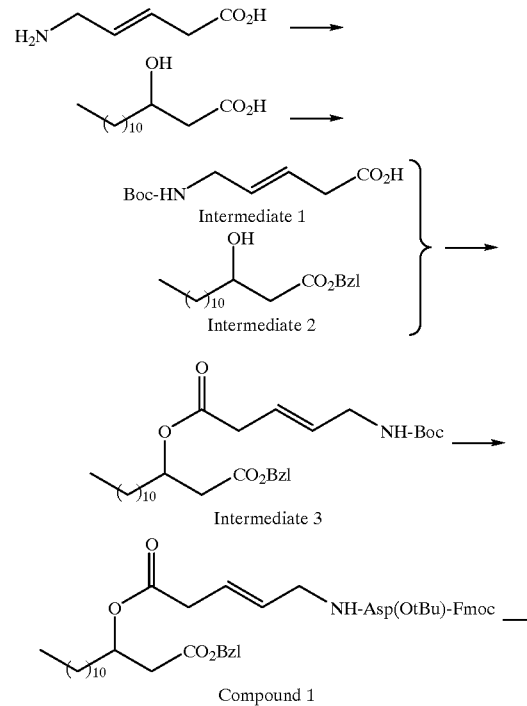

Compound 1

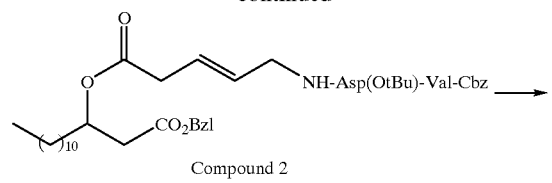

Compound 2

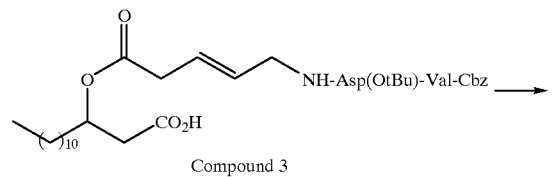

Compound 3

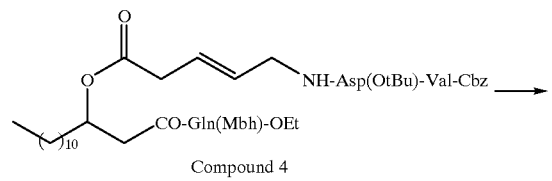

Compound 4

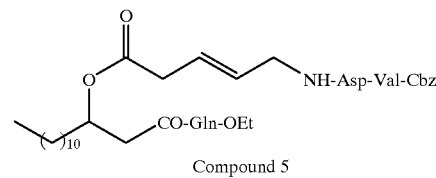

Compound 5

Reaction Scheme 2

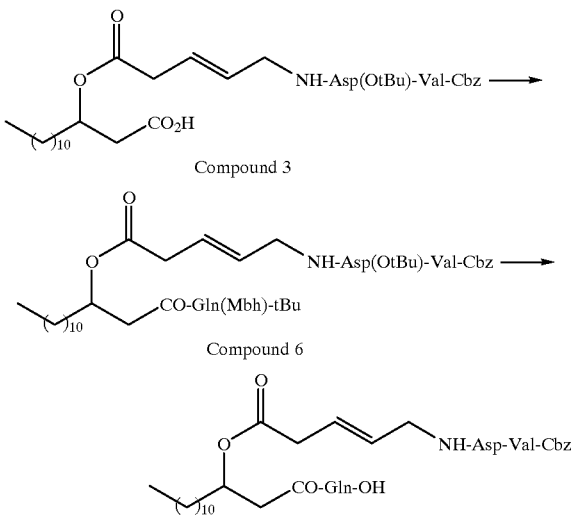

Compound 3

Compound 6

Compound 7

Reaction Scheme 3
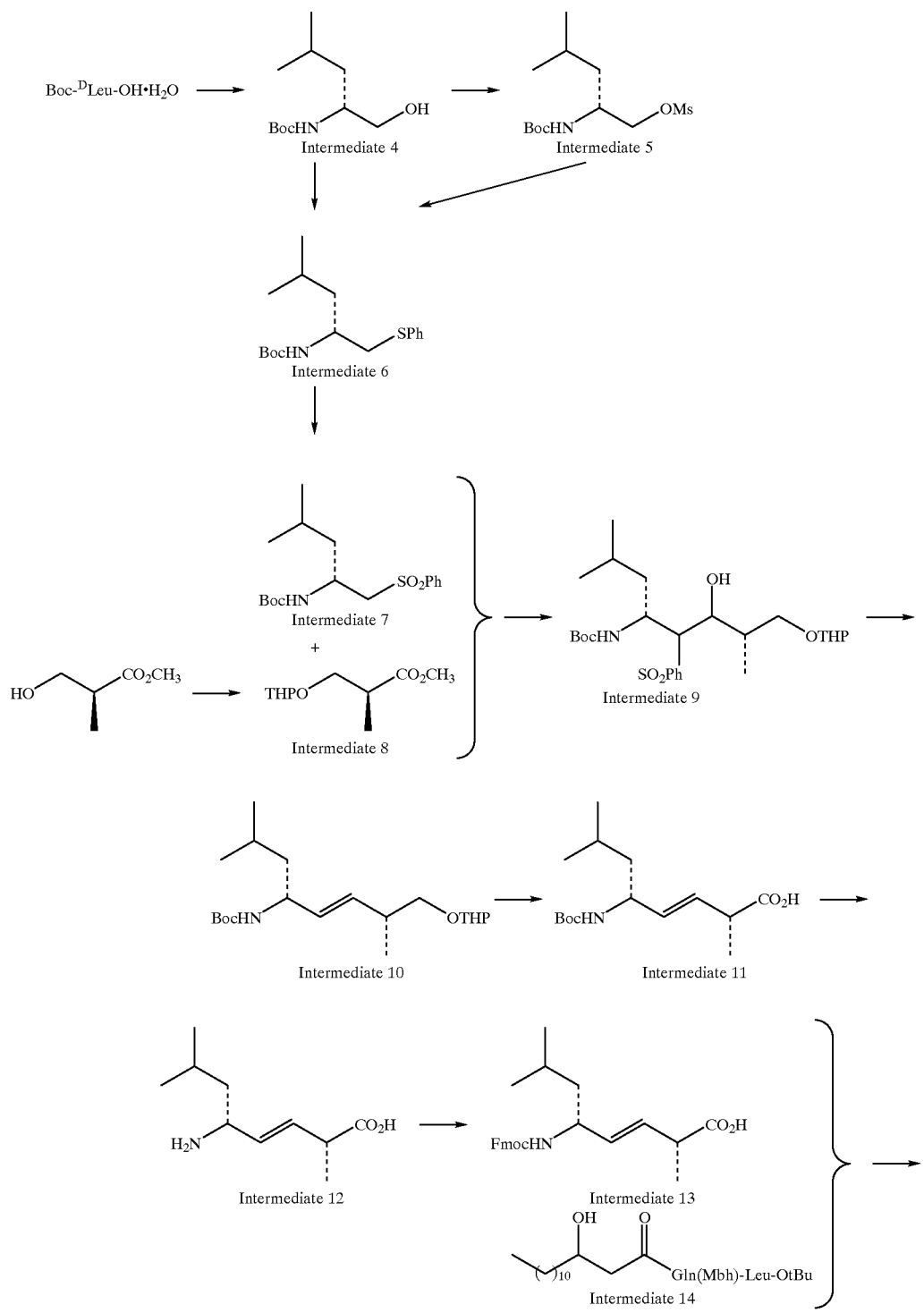

-continued
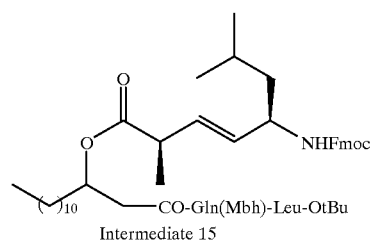
Intermediate 15
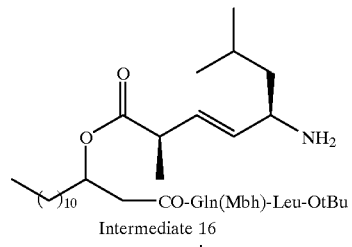
Intermediate 16
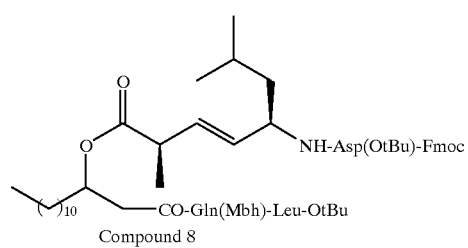
Compound 8
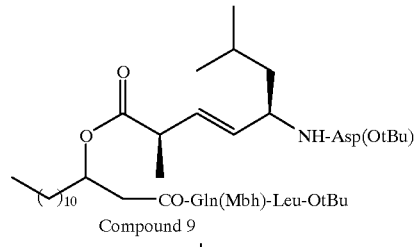
Compound 9
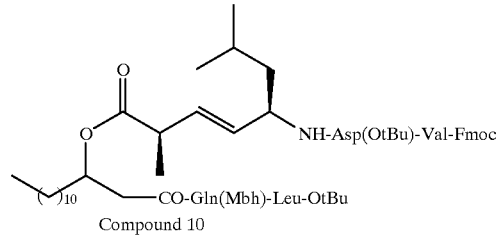
Compound 10

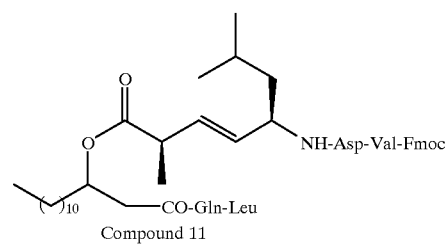
Compound 11
Reaction Scheme 4
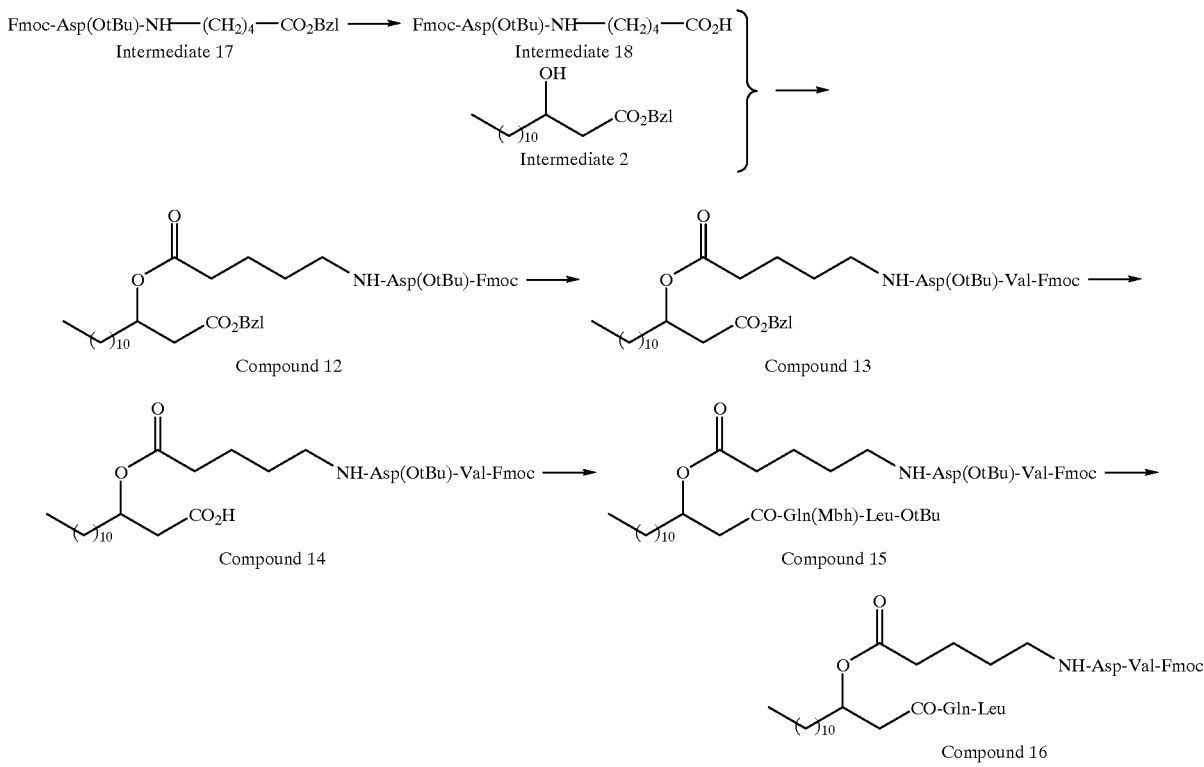
Reaction Scheme 5
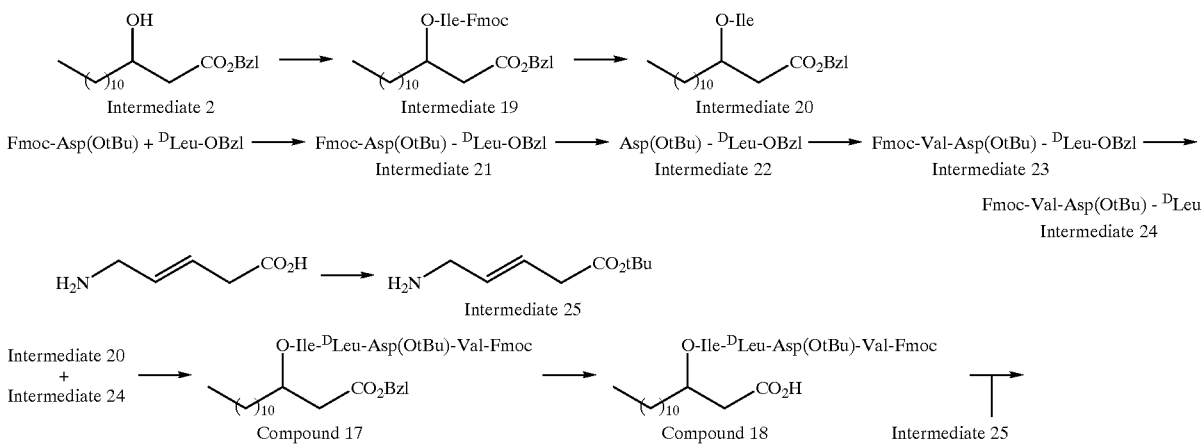

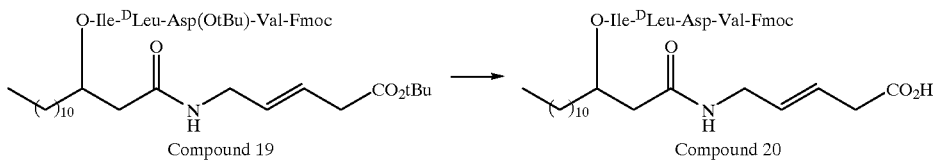

Compound 19 → Compound 20

Reaction Scheme 6

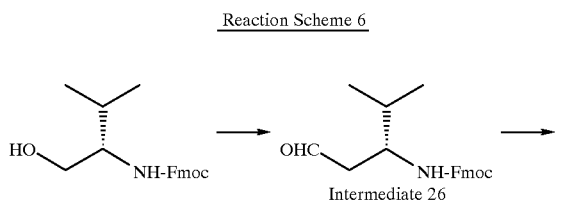

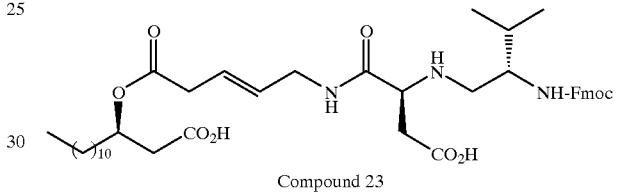

Compound 21 → Compound 22 → Compound 23

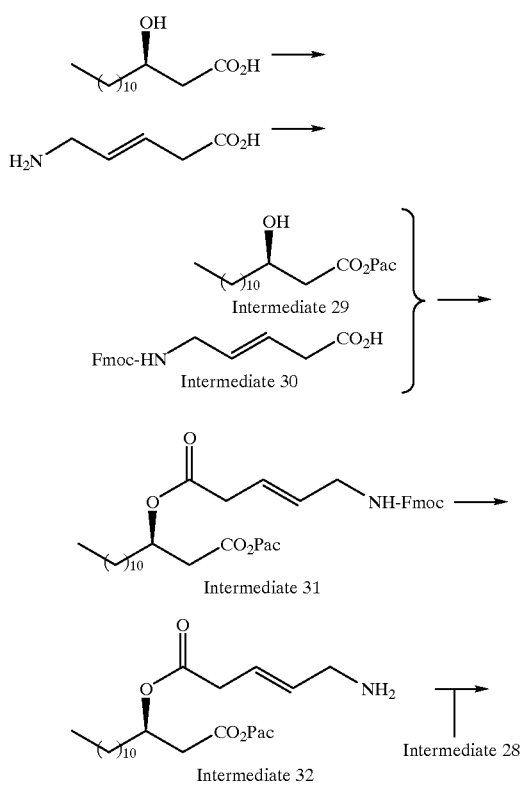

EXAMPLE 1

1-i)

To a mixed solution of 5-amino-3-pentenoic acid (1.00 g) in dioxane (17 ml), water (8.7 ml) and 1M aqueous sodium carbonate (8.7 ml) was added under ice-cooling di-t-butyl dicarbonate (2.09 g). The solution was stirred at room temperature for 5 hours and then concentrated under reduced pressure to about 15 ml. The resultant solution was adjusted to pH of about 3 under ice-cooling with 10% aqueous citric acid. The aqueous layer was extracted with ethyl acetate and the combined organic layers were washed with water and dried over anhydrous sodium sulfate. After the solvent was removed in vacuo, the residue was recrystallized from ethyl acetate-hexane to afford 1.81 g of 5-Boc amino-3-pentenoic acid (Intermediate 1).

$^1$H-NMR (δ ppm, CDCl$_3$): 6.10 (1H, br s), 5.55–5.75 (2H, m), 4.66 (1H, br s), 3.65–3.80 (2H, m), 3.11 (2H, d, J=6.4 Hz), 1.45 (9H, s).

1-ii)

To a solution of 5.00 g of 3-hydroxymyristic acid in 50 ml of DMF were added at room temperature 2.85 ml of triethylamine and 2.43 ml of benzyl bromide. The reaction mixture was stirred at room temperature overnight. The solvent was removed in vacuo, ethyl acetate and water were added to the residue, and the organic layer was separated, washed twice with water and dried over anhydrous sodium sulfate. After the solvent was removed in vacuo, the crude product was purified by a silica gel column chromatography to afford 3.69 g of benzyl 3-hydroxymyristate (Intermediate 2).

$^1$H-NMR (δ ppm, CDCl$_3$) 7.33–7.40 (m, 5H), 5.16 (s, 2H), 3.95–4.05 (m, 1H), 2.85 (d, J=4.4 Hz, 1H), 2.56 (dd, J=2.9, 17 Hz, 1H), 2.46 (dd, J=9.0, 17 Hz, 1H), 1.20–1.60 (m, 20H), 0.88 (t, J=6.8 Hz, 3H).

1-iii)

To a solution of Intermediate 1 (1.00 g), Intermediate 2 (1.55 g) and dimethylaminopyridine (40 mg) in dichloromethane (40 ml) was added under ice-cooling DCC (1.44 g). The resulting mixture was stirred under ice-cooling for 2 hours and then at room temperature overnight. After the precipitate was filtered off, the dichloromethane was removed in vacuo. To the residue were added ethyl acetate and 10% aqueous citric acid. The separated ethyl acetate layer was washed successively with water, 5% aqueous sodium hydrogencarbonate and water and dried over anhydrous sodium sulfate. After the ethyl acetate was removed in vacuo, the residue was purified by a silica gel column chromatography to afford 2.29 g of Intermediate 3.

$^1$H-NMR (δ ppm, CDCl$_3$): 7.30–7.40 (5H, m), 5.50–5.68 (2H, m), 5.20–5.25 (1H, m), 5.11 (2H, s), 4.59 (1H, br s), 3.71 (2H, br s), 2.96 (2H, d, J=4.9 Hz), 2.57–2.66 (2H, m), 1.50–1.65 (2H, m), 1.44 (9H, s), 1.20–1.35 (18H, m), 0.88 (3H, t, J=6.8 Hz).

1-iv)

A solution of Intermediate 3 (1.29 g) in trifluoroacetic acid (hereinafter referred to as "TFA") (13 ml) was stirred at room temperature for 30 minutes. After the TFA was removed in vacuo, the residue was dissolved in ethyl acetate, washed with saturated aqueous sodium hydrogencarbonate and dried over anhydrous sodium sulfate. The ethyl acetate was removed in vacuo to afford an amine derivative. To a solution of the amine derivative thus obtained, Fmoc-L-aspartic acid P-t-butyl ester (Fmoc-Asp(OtBu)) (1.00 g) and HOBT-monohydrate (0.41 g) in dichloromethane (30 ml) was added under ice-cooling WSCI (0.51 g). The resulting solution was stirred under ice-cooling for 2 hours and then at room temperature overnight. After the dichloromethane was removed in vacuo, the residue was dissolved in ethyl acetate and the solution was washed successively with 10% aqueous citric acid, water, 5% aqueous sodium hydrogencarbonate and water and then dried over anhydrous sodium sulfate. After the ethyl acetate was removed in vacuo, the residue was purified by a silica gel column chromatography to afford 1.59 g of Compound 1.

$^1$H-NMR (δ ppm, CDCl$_3$): 7.76 (2H, d, J=7.3 Hz), 7.58 (2H, d, 7.3 Hz), 7.40 (2H, t, 7.3 Hz), 7.27–7.35 (7H, m), 6.53 (1H, br s), 5.94 (1H, d, J=7.8 Hz), 5.62–5.67 (1H, m), 5.45–5.55 (1H, m), 5.19–5.26 (1H, m), 5.10 (2H, s), 4.50 (1H, br s), 4.43 (2H, d, J=6.8 Hz), 4.22 (1H, t, J=6.8 Hz), 3.80–3.85 (2H, m), 2.94 (2H, d, J=6.8 Hz), 2.89 (1H, br s), 2.50–2.65 (3H, m), 1.50–1.65 (2H, m), 1.44 (9H, s), 1.20–1.35 (18H, m), 0.88 (3H, t, J=6.8 Hz).

1-v)

To a solution of Compound 1 (1.59 g) in DMF (21 ml) was added diethylamine (2.1 ml) and the resulting mixture was stirred at room temperature for 4 hours. After the solvent was removed in vacuo, the crude product thus obtained was purified by a silica gel column chromatography to afford 0.92 g of an amine derivative. To a solution of the amine derivative thus obtained (0.5 g), Cbz-L-valine (0.21 g) and HOBt.monohydrate (0.14 g) in dichloromethane (30 ml) was added under ice-cooling WSCI (0.17 g). The solution was stirred under ice-cooling for 2 hours and then at room temperature overnight. After the dichloromethane was removed in vacuo, to the residue were added ethyl acetate and 10% aqueous citric acid. The separated ethyl acetate layer was washed successively with water, 5% aqueous sodium hydrogencarbonate and water and dried over anhydrous sodium sulfate. After the ethyl acetate was removed in vacuo, the residue was purified by a silica gel column chromatography to afford 0.63 g of Compound 2.

$^1$H-NMR (δ ppm, CD$_3$OD): 7.25–7.35 (10H, m), 5.45–5.70 (2H, m), 5.15–5.25 (1H, m), 5.05–5.15 (4H, m), 4.60–4.70 (1H, m), 3.85–3.90 (2H, m), 3.65–3.75 (1H, m), 2.55–2.90 (6H, m), 2.00–2.10 (1H, m), 1.50–1.65 (2H, m), 1.43 (9H, s), 1.20–1.45 (18H, m), 0.80–1.00 (9H, m).

1-vi)

To a solution of Compound 2 (0.53 g) in methanol (15 ml) were added ammonium formate (0.24 g) and 5% palladium-carbon (25 mg), and the mixture was stirred at about 70° C. for 4 hours. After the palladium-carbon was filtered off, the methanol was removed in vacuo. The crude product was purified by a silica gel column chromatography to afford 0.28 g of Compound 3.

$^1$H-NMR (δ ppm, CD$_3$OD): 7.25–7.40 (5H, m), 5.50–5.75 (2H, m), 5.15–5.30 (1H, m), 5.11, 5.10 (2H, 2s), 4.60–4.70 (1H, m), 3.85–3.90 (1H, m), 3.70–3.80 (2H, m), 2.35–3.05 (6H, m), 2.00–2.15 (1H, m), 1.50–1.65 (2H, m), 1.43, 1.44 (9H, 2s), 1.20–1.40 (18H, m), 0.85–1.05 (9H, m).

1-vii)

To a solution of Compound 3 (0.14 g), N-γ-Mbh-L-glutamine ethyl ester (Gln(Mbh)-OEt) (75 mg) and HOBt-monohydrate (32 mg) in dichloromethane (10 ml) was added under ice-cooling WSCI (40 mg). The solution was stirred under ice-cooling for 2 hours and then at room temperature overnight. After the dichloromethane was removed in vacuo, to the residue were added ethyl acetate and 10% aqueous citric acid. The separated ethyl acetate layer was washed successively with water, 5% aqueous sodium hydrogencarbonate and water and dried over anhydrous sodium sulfate. After the ethyl acetate was removed in vacuo, the residue was purified by a silica gel column chromatography to afford 0.08 g of Compound 4.

$^1$H-NMR (δ ppm, CD$_3$OD): 7.25–7.40 (5H, m), 7.10–7.15 (4H, m), 6.85 (4H, d, J=8.8 Hz), 6.08 (1H, s), 5.45–5.70 (2H, m), 5.15–5.25 (1H, m), 5.09 (2H, s), 4.60–4.75 (1H, m), 4.30–4.40 (1H, m), 4.10–4.20 (2H, m), 3.88 (1H, d, J=6.4 Hz), 3.76 (6H, s), 3.60–3.80 (2H, m), 2.95–3.05 (2H, m), 2.25–2.85 (6H, m), 1.90–2.20 (3H, m), 1.50–1.70 (2H, m), 1.42, 1.43 (9H, 2s), 1.20–1.45 (21H, m), 0.85–1.00 (9H, m).

1-viii)

A solution of Compound 4 (0.08 g) in TFA (2 ml) was stirred at room temperature for 3.5 hours. After the TFA was removed in vacuo, to the residue were added ethyl acetate and 5% aqueous sodium hydrogencarbonate. The separated aqueous layer was washed with ethyl acetate and then adjusted to pH about 4 with conc. hydrochloric acid. The solid thus formed was recovered by filtration and dried to afford 0.02 g of Compound 5.

$^1$H-NMR (δ ppm, CD$_3$OD): 7.25–7.40 (5H, m), 5.65–5.75 (1H, m), 5.50–5.60 (1H, m), 5.15–5.30 (1H, m), 5.11 (2H, 2s), 4.65–4.75 (1H, m), 4.35–4.45 (1H, m), 4.10–4.20 (2H, m), 3.90 (1H, d, J=6.4 Hz), 3.60–3.80 (2H, m), 3.00–3.10 (2H, m), 2.00–3.00 (8H, m), 1.85–2.00 (1H, m), 1.55–1.70 (2H, m), 1.20–1.40 (21H, m), 0.85–1.05 (9H, m).

1-ix)

The Gln(Mbh)-OEt which was used in the above synthesis route for Compound 4 was synthesized as follows.

To a suspension of N-α-Cbz-N-γ-Mbh-L-glutamine (Cbz-Gln(Mbh)) (5.00 g) and sodium hydrogencarbonate (1.66 g) in DMF (50 ml) was added dropwise a solution of ethyl bromide (7.52 ml) in DMF (50 ml) at room temperature. The reaction solution was stirred at room temperature overnight and then water was added. The aqueous layer was extracted with ethyl acetate, the combined organic layers were washed with water and dried over anhydrous sodium sulfate. After the solvent was removed in vacuo, the crude product thus obtained was recrystallized from ethyl acetate-hexane to afford 4.62 g of Cbz-Gln(Mbh)-OEt.

$^1$H-NMR (δ ppm, CDCl$_3$): 7.27–7.40 (5H, m), 7.14 (4H, dd, J=6.1, 7.8 Hz), 6.84 (4H, dd, J=0.92, 8.8 Hz), 6.45 (1H, d, J=7.8 Hz), 6.14 (1H, d, J=7.8 Hz), 5.60 (1H, d, J=7.8 Hz), 5.09 (2H, s), 4.29–4.38 (1H, m), 4.11–4.22 (2H, m), 3.78 (6H, s), 2.19–2.40 (3H, m), 1.90–2.02 (1H, m), 1.25 (3H, t, J=7.1 Hz).

To a solution of the Cbz-Gln(Mbh)-OEt (2.62 g) in methanol (50 ml) was added 5% palladium-carbon (0.26 g) and the resulting mixture was stirred at room temperature under hydrogen atmosphere for 4 hours. After the palladium-carbon was filtered off, the methanol was removed in vacuo, and the resulting crude product was recrystallized from ethyl acetate-hexane to afford 1.95 g of Gln(Mbh)-OEt.

$^1$H-NMR (δ ppm, CDCl$_3$): 7.13 (4H, d, J=8.8 Hz), 6.85 (4H, td, J=2.6, 8.8 Hz), 6.52 (1H, d, J=7.8 Hz), 6.14 (1H, d, J=7.8 Hz), 4.16 (2H, q, J=7.2 Hz), 3.79 (6H, s), 3.40–3.47 (1H, m), 2.33–2.48 (2H, m), 2.08–2.20 (1H, m), 1.78–1.89 (1H, m), 1.56 (2H, s), 1.26 (3H, t, J=7.3 Hz).

EXAMPLE 2

2-i)

To a solution of Compound 3 (120 mg), Gln(MbH)-OtBu (86 mg) and HOBT-monohydrate (25 mg) in dichloromethane (10 ml) was added WSCI (31 mg) under ice-cooling. The solution was stirred under ice-cooling for 2 hours and then at room temperature overnight. After the dichloromethane was removed in vacuo, to the residue were added ethyl acetate and 10% aqueous citric acid. The separated ethyl acetate layer was washed successively with water, 5% aqueous sodium hydrogencarbonate and water and dried over anhydrous sodium sulfate. After the ethyl acetate was removed in vacuo, the residue was purified by a silica gel column chromatography to afford 0.08 g of Compound 6.

$^1$H-NMR (δ ppm, CD$_3$OD): 7.28–7.41 (8H, m), 7.11–7.18 (4H, m), 6.62–6.96 (6H, m), 6.16 (1H, d, J=8.3 Hz), 5.53–5.78 (1H, m), 5.12–5.53 (2H, m), 5.05–5.12 (2H, m), 4.65–4.76 (1H, m), 4.39–4.49 (1H, m), 3.96–4.05 (1H, m), 3.63–3.85 (8H, m), 2.78–3.04 (2H, m), 2.52–2.67 (1H, m), 2.08–2.51 (7H, m), 1.73–1.96 (1H, m), 1.51–1.67 (2H, m), 1.33–1.50 (18H, m), 1.21–1.33 (18H, m), 0.85–1.00 (9H, m).

2-ii)

A solution of Compound 6 (0.08 g) in TFA (2 ml) was stirred at room temperature for one hour. After the solvent was removed in vacuo, to the residue were added ethyl acetate and 5% aqueous sodium hydrogencarbonate. The separated aqueous layer was adjusted to pH of about 4 with conc. hydrochloric acid. The solid thus formed was recovered by filtration and dried to afford 0.01 g of Compound 7.

$^1$H-NMR (δ ppm, CD$_3$OD): 7.23–7.39 (5H, m), 5.65–5.74 (1H, m), 5.50–5.59 (1H, m), 5.17–5.29 (1H, m), 5.11 (1H, s), 5.10 (1H, s), 4.64–4.74 (1H, m), 4.32–4.40 (1H, m), 3.87–3.92 (1H, m), 3.68–3.79 (2H, m), 3.01–3.07 (1H, m), 2.72–2.91 (2H, m), 2.45–2.56 (2H, m), 2.22–2.40 (3H, m), 2.04–2.19 (2H, m), 1.89–1.99 (1H, m), 1.55–1.67 (2H, m), 1.21–1.37 (18H, m), 0.86–1.07 (9H, m).

2-iii)

The Gln(Mbh)-OtBu which was used in the above synthesis route for Compound 6 was synthesized as follows.

To a suspension of N-α-Cbz-N-γ-Mbh-L-glutamine (Cbz-Gln(Mbh)) (3.00 g), tert-butyl alcohol (0.62 ml) and dimethylaminopyridine (0.36 g) in DMF (20 ml) was added WSCI (1.25 g) under ice-cooling. The solution was stirred under ice-cooling for 2 hours and then at room temperature overnight. After the DMF was removed in vacuo, to the residue were added ethyl acetate and 10% aqueous citric acid. The separated ethyl acetate layer was washed successively with water, 5% aqueous sodium hydrogencarbonate and water and dried over anhydrous sodium sulfate. After the ethyl acetate was removed in vacuo, the residue was purified by a silica gel column chromatography and recrystallization from ethyl acetate-hexane to afford 1.28 g of N-α-Cbz-N-γ-Mbh-L-glutamine-t-butyl ester (Cbz-Gln-(Mbh)-OBu).

$^1$H-NMR (δ ppm, CDCl$_3$): 7.24–7.39 (5H, m), 7.04–7.20 (4H, m), 6.76–6.88 (4H, m), 6.57 (1H, d, J=7.3 Hz), 6.13 (1H, d, J=8.3 Hz), 5.52 (1H, d, J=8.3 Hz), 5.08 (2H, s), 4.16–4.26 (1H, m), 3.78 (6H, s), 2.12–2.41 (3H, m), 1.84–2.06 (1H, m), 1.44 (9H, s).

To a solution of the Cbz-Gln(Mbh)-OBu (0.11 g) in methanol (5 ml) was added 5% palladium-carbon (10 mg) and the resulting mixture was stirred under hydrogen atmosphere for 4 hours. The palladium-carbon was filtered off and then the methanol was removed in vacuo to afford Gln(Mbh)-OBu.

EXAMPLE 3

3-i)

To a solution of N-t-butylcarbonyl-D-leucine.monohydrate (Boc-D-Leu-OH-H$_2$O) (2.5 g) in THF (12 ml) was added triethylamine (1.25 g) and then ethyl chloroformate (1.09 g) was added under ice-cooling. The solution was stirred under ice-cooling for 30 minutes and then filtered. To the filtrate was gradually added under ice-cooling a suspension of NaBH$_4$ (946 mg) in water (12 ml). The resulting solution was stirred under ice-cooling for 4 hours and ether (100 ml) was added. The aqueous layer was extracted three times with chloroform (200 ml) and the combined organic layers were dried over anhydrous sodium sulfate. After the solvent was removed in vacuo, the residue was purified by a silica gel column chromatography to afford 1.35 g of Intermediate 4.

$^1$H-NMR (δ ppm, CDCl$_3$): 4.55 (1H, br s), 3.64–3.72 (2H, m), 3.47–3.52 (1H, m), 2.43 (1H, br s), 1.61–1.72 (1H, m), 1.24–1.36 (2H, m), 1.45 (9H, s), 0.92–0.95 (6H, m).

3-ii)

To a solution of Intermediate 4 (1.35 g) and triethylamine (1.9 g) in dichloromethane (40 ml) was added under ice-cooling mesyl chloride (1.78 g). The solution was stirred under ice-cooling for one hour and then chloroform (100 ml) was added and washed twice with water (50 ml). The organic layer was dried over anhydrous sodium sulfate. After the solvent was removed in vacuo, the residue was purified by a silica gel column chromatography to afford 1.76 g of Intermediate 5.

$^1$H-NMR (δ ppm, CDCl$_3$): 4.50–4.56 (1H, m), 4.16 (1H, br d, J=4.0 Hz), 4.15 (1H, dd, J=4.0, 10 Hz), 3.92 (1H, br s), 3.03 (3H, s), 1.65–1.73 (1H, m), 1.44 (9H, s), 1.28–1.45 (2H, m), 0.94 (3H, d, J=3.2 Hz), 0.93 (3H, d, J=3.2 Hz).

3-iii)

To a solution of sodium methoxide (1.03 g) and thiophenol (2.17 g) in THF (8 ml) and methanol (3 ml) was added a solution of Intermediate 4 (1.76 g) in THF (7 ml). The solution was stirred at 50° C. for 4 hours and then chloroform (50 ml) and 10% aqueous sodium hydroxide (15 ml) were added. The organic layer was washed with 5% aqueous sodium hydroxide and saturated aqueous sodium bicarbonate and then dried over anhydrous sodium sulfate. After the solvent was removed in vacuo, the residue was purified by a silica gel column chromatography to afford 1.77 g of Intermediate 6.

$^1$H-NMR (δ ppm, CDCl$_3$): 7.37–7.40 (2H, m), 7.26–7.29 (2H, m), 7.15–7.19 (1H, m), 4.50–4.57 (1H, m), 3.75–3.91 (1H, m), 2.93–3.10 (2H, m), 1.57–1.65 (1H, m), 1.41 (9H, s), 1.38–1.48 (2H, m), 0.90 (3H, d, J=6.4 Hz), 0.87 (3H, d, J=6.4 Hz).

3-iv)

As an alternative method, to a solution of Intermediate 4 (1.20 g) in THF (15 ml) were added under ice-cooling diphenyl disulfide (1.88 g) and tri-n-butyl phosphine (1.68 g). The solution was stirred at room temperature for 16 hours. After the solvent was removed in vacuo, the residue was purified by a silica gel column chromatography to afford 1.70 g of Intermediate 6.

3-v)

To a solution of Intermediate 6 (1.70 g) in dichloromethane (45 ml) was added under ice-cooling mCPBA (3.03 g). The solution was stirred under ice-cooling for one hour and then chloroform (50 ml) and 15% aqueous sodium hydroxide (15 ml) were added and aqueous sodium bisulfite (15 ml) was then added. The aqueous layer was extracted twice with chloroform (20 ml) and the combined organic layers were dried over anhydrous sodium sulfate. After the solvent was removed in vacuo, the residue was crystallized from hexane-ethyl acetate to afford 1.74 g of Intermediate 7.

$^1$H-NMR (δ ppm, CDCl$_3$): 7.91–7.94 (2H, m), 7.64 (1H, m), 7.55–7.59 (2H, m), 4.82 (1H, br s), 3.94–4.01 (1H, m), 3.41–3.44 (1H, m), 3.23–3.28 (1H, m), 1.50–1.72 (3H, m), 1.40 (9H, s), 0.87–0.90 (6H, m).

3-vi)

To a solution of methyl 1-methyl-(S)-2-hydroxypropionate (1.18 g) and dihydropyran (1.10 g) in dichloromethane (20 ml) was added at room temperature p-toluenesulfonic acid (50 mg). The solution was stirred at room temperature for 4 hours and then chloroform (100 ml) and water (80 ml) were added. The aqueous layer was extracted twice with chloroform (20 ml) and the combined organic layers were dried over anhydrous sodium sulfate. After the solvent was removed in vacuo, the residue was purified by a silica gel column chromatography to afford 2.03 g of Intermediate 8.

$^1$H-NMR (δ ppm, CDCl$_3$): 4.60 and 4.62 (1H, t, J=3.2 Hz), 3.74–3.94 (2H, m), 3.70 (s, 3H), 3.42–3.62 (2H, m), 2.74 (1H, m), 1.52–1.80 (6H, m), 1.18 and 1.20 (3H, d, J=6.8 Hz).

3-vii)

To a solution of Intermediate 7 (683 mg) in THF (24 ml) was added at −78° C. methyl lithium (in diethyl ether, 1.03M) (4.27 ml). The solution was stirred at −78° C. for 30 minutes (Solution A). To a solution of Intermediate 8 (971 mg) in diethyl ether (14 ml) was added dropwise at −78° C. DIBAH (in a hexane solution, 0.95M) (5.5 ml). The solution was stirred at −78° C. for 30 minutes (Solution B). Solution B was added to Solution A by means of a cannula and the resulting solution was stirred at −78° C. for 30 minutes. To the solution were added diethyl ether (100 ml), water (80 ml) and saturated aqueous ammonium chloride (100 ml) and it was allowed to rise to a room temperature and then saturated aqueous Rochelle salt (100 ml) was added. The aqueous layer was extracted twice with diethyl ether (100 ml) and the combined organic layers were washed successively with saturated aqueous Rochelle salt, saturated aqueous ammonium chloride, water and saturated aqueous sodium chloride and then dried over anhydrous sodium sulfate. After the solvent was removed in vacuo, the resulting compound was used as Intermediate 9 for subsequent reaction.

3-viii)

To a solution of Intermediate 9 thus obtained in methanol (40 ml) were added sodium phosphate (3.25 g) and 5% sodium amalgam (12.5 g) under ice-cooling. The solution was stirred under ice-cooling for 4 hours and then filtered. After the filtrate was concentrated under reduced pressure, diethyl ether (100 ml) was added and washed twice with water (50 ml). The organic layer was dried over anhydrous sodium sulfate. After the solvent was removed in vacuo, the residue was purified by a silica gel column chromatography to afford 330 mg of Intermediate 10.

$^1$H-NMR (δ ppm, CDCl$_3$): 5.51–5.59 (1H, m), 5.31–5.41 (1H, m), 4.55–4.60 (1H, m), 4.25–4.41 (1H, m), 4.00–4.16 (1H, m), 3.81–3.88 (1H, m), 3.45–3.63 (2H, m), 3.17–3.30 (1H, m), 2.41–2.49 (1H, m), 1.39 (9H, s), 1.23–1.87 (9H, m), 1.02 and 1.03 (3H, d, J=4.4 Hz), 0.92 (3H, d, 4.4 Hz), 0.90 (3H, d, J=4.4 Hz).

3-ix)

To a solution of Intermediate 10 (330 mg) in acetone (50 ml) was added under ice-cooling Jones reagent (1.92M) (1.6 ml). The solution was stirred under ice-cooling for 2 hours and then water (100 ml) and diethyl ether (50 ml) were added. The aqueous layer was extracted twice with diethyl ether (50 ml) and the combined organic layers were washed three times with 5% aqueous sodium hydroxide (50 ml). To the aqueous layer was added 3N aqueous hydrochloric acid so as to adjust the pH to 3–4, extracted three times with diethyl ether (50 ml) and the combined organic layers were dried over anhydrous sodium sulfate. After the solvent was removed in vacuo, the resulting compound was used as Intermediate 11 for subsequent reaction.

3-x)

To Intermediate 11 thus obtained was added TFA (3 ml) and the mixture was stirred at room temperature for 2 hours. After the solvent was removed in vacuo, the resulting compound was used as Intermediate 12 for subsequent reaction.

3-xi)

To a solution of Intermediate 12 thus obtained in 10% aqueous sodium carbonate (6 ml) was added a solution of Fmoc-Cl (365 mg) in dioxane (6 ml). The solution was stirred at room temperature for 4 hours and then isopropyl ether (20 ml) and water (10 ml) were added. The aqueous layer was washed with isopropyl ether, 3N aqueous hydrochloric acid was added until the pH was adjusted to 3 and extracted with ethyl acetate. The organic layer was dried over anhydrous sodium sulfate. After the solvent was removed in vacuo, the residue was purified by a silica gel column chromatography to afford 50 mg of Intermediate 13.

$^1$H-NMR (δ ppm, CDCl$_3$): 7.73–7.75 (2H, m), 7.56–7.58 (2H, m), 7.36–7.37 (2H, m), 7.27–7.31 (2H, m), 5.28–5.76 (2H, m), 4.63–4.75 (1H, m), 4.34–4.54 (2H, m), 4.13–4.28 (2H, m), 2.96–3.22 (1H, m), 1.50–1.67 (1H, m), 1.14–1.43 (5H, m), 0.69–0.99 (6H, m).

3-xii)

To a solution of Intermediate 13 (160 mg) and Intermediate 14 (369 mg) in dichloromethane (5 ml) were added under ice-cooling dimethylaminopyridine (10 mg) and DCC (99 mg). The solution was stirred at room temperature for 6 hours and filtered with Celite. After the solvent was removed in vacuo, chloroform was added and the mixture was washed successively with water, 5% aqueous sodium hydrogencarbonate, 10% aqueous citric acid and saturated aqueous sodium chloride. After it was dried over anhydrous sodium sulfate, the solvent was removed in vacuo, and the residue was purified by a silica gel column chromatography to afford 310 mg of Intermediate 15.

$^1$H-NMR (δ ppm, CDCl$_3$): 7.71–7.81 (2H, m), 7.52–7.69 (2H, m), 7.09–7.43 (8H, m), 6.48–6.89 (5H, m), 6.07–6.28 (1H, m), 5.35–5.78 (1H, m), 5.05–5.28 (1H, m), 3.98–4.48 (7H, m), 3.76 and 3.78 (3H, s), 3.75 and 3.76 (3H, s), 3.41–3.54 (1H, m), 1.41 and 1.42 (9H, s), 1.02–2.46 (3H, m), 0.67–0.96 (15H, m).

3-xiii)

To a solution of Intermediate 15 (310 mg) in DMF (3 ml) was added at room temperature diethylamine (0.3 ml). The solution was stirred at room temperature for 2.5 hours. After the solvent was removed in vacuo, the residue was purified by a silica gel column chromatography to afford 200 mg of Intermediate 16.

$^1$H-NMR (δ ppm, CDCl$_3$): 7.60–7.69 (1H, m), 7.12–7.25 (4H, m), 6.63–6.88 (5H, m), 6.15–6.23 (1H, m), 5.59–5.76 (1H, m), 5.38–5.53 (1H, m), 5.13–5.22 (1H, m), 4.25–4.46 (2H, m), 3.78 and 3.79 (3H, s), 3.76 and 3.78 (3H, s), 3.29–3.41 (1H, m), 3.00–3.16 (1H, m), 2.32–2.77 (4H, m), 1.40 and 1.42 (9H, s), 1.17–1.67 (31H, m), 0.82–0.94 (15H, m).

3-xiv)

To a solution of Intermediate 16 (200 mg) and Fmoc-L-aspartic acid P-t-butyl ester (FmocASp(OtBu)) (106 mg) in dichloromethane (5 ml) were added HOBt.monohydrate (35 mg) and WSCI (50 mg) under ice-cooling. The solution was stirred at room temperature for 66 hours, the solvent was removed in vacuo and the residue was dissolved in chloroform. The solution was washed successively with water, 5% aqueous sodium hydrogencarbonate, 10% aqueous citric acid and saturated aqueous sodium chloride. After it was dried over anhydrous sodium sulfate, the solvent was removed in vacuo, and the residue was purified by a silica gel column chromatography to afford 220 mg of Compound 8.

$^1$H-NMR (δ ppm, CDCl$_3$): 7.72–7.79 (2H, m), 7.51–7.62 (m, 2H), 7.27–7.43 (4H, m), 7.03–7.24 (5H, m), 6.56–6.87 (6H, m), 6.07–6.48 (2H, m), 5.54–5.75 (1H, m), 5.35–5.49 (1H, m), 5.09–5.22 (1H, m), 4.17–4.73 (7H, m), 3.76 and 3.77 (3H, s), 3.76 (3H, s), 1.88–3.08 (7H, m), 1.42 and 1.43 (9H, s), 1.41 and 1.42 (9H, s), 1.09–1.70 (31H, m), 0.71–0.92 (15H, m).

3-xv)

To a solution of Compound 8 (220 mg) in DMF (2 ml) was added at room temperature diethylamine (0.2 ml). The solution was stirred at room temperature for 2.5 hours. After the solvent was removed in vacuo, the residue was purified by a silica gel column chromatography to afford 160 mg of Compound 9.

$^1$H-NMR (δ ppm, CDCl$_3$): 7.27–7.58 (2H, m), 7.12–7.25 (4H, m), 6.62–7.01 (6H, m), 6.19–6.25 (1H, m), 5.55–5.77 (1H, m), 5.39–5.51 (1H, m), 5.12–5.25 (1H, m), 4.25–4.47 (3H, m), 3.79 and 3.79 (6H, s), 3.58–3.70 (1H, m), 2.99–3.10 (1H, m), 2.78–2.87 (1H, m), 2.28–2.51 (5H, m), 1.45 (9H, 2s), 1.43 (9H, s), 1.15–2.15 (31H, m), 0.82–0.93 (15H, m).

3-xvi)

To a solution of Compound 9 (160 mg) and Fmoc-L-valine (59 mg) in dichloromethane (3 ml) were added HOBt-monohydrate (24 mg) and WSCI (33 mg) under ice-cooling. The solution was stirred at room temperature for 16 hours, the solvent was removed in vacuo and the residue was dissolved in chloroform. The solution was washed successively with water, 5% aqueous sodium hydrogencarbonate, 10% aqueous citric acid and saturated aqueous sodium chloride. After it was dried over anhydrous sodium sulfate, the solvent was removed in vacuo, and the residue was purified by a silica gel column chromatography to afford a crude product. This product was solidified with chloroform-ethyl acetate-hexane to afford 200 mg of Compound 10.

$^1$H-NMR (δ ppm, CDCl$_3$): 7.73–7.80 (2H, m), 7.27–7.61 (8H, m), 7.09–7.23 (5H, m), 6.60–6.97 (6H, m), 6.18–6.26 (1H, m), 5.31–5.73 (3H, m), 5.09–5.23 (1H, m), 4.75–4.96 (1H, m), 4.15–4.52 (6H, m), 3.96–4.11 (1H, m), 3.76 (3H, 2s), 3.74 and 3.76 (3H, s), 2.17–3.04 (7H, m), 1.08–2.15 (32H, m), 0.75–1.00 (21H, m).

3-xvii)

Compound 10 (200 mg) was dissolved in TFA (3 ml). The solution was stirred at room temperature for 3 hours. After the solvent was removed in vacuo, the residue was solidified with chloroform-methanol-diethyl ether to afford 70 mg of Compound 11.

$^1$H-NMR (δ ppm, CDCl$_3$): 7.79 (2H, d, J=7.6 Hz), 7.41–7.75 (2H, m), 7.39 (2H, t, J=7.6 Hz), 7.32 (2H, t, J=7.6 Hz), 5.54–5.70 (1H, m), 5.38–5.49 (1H, m), 5.10–5.25 (1H, m), 4.65–4.80 (1H, m), 4.20–4.50 (6H, m), 3.83–3.90 (1H, m), 2.71–3.04 (3H, m), 2.22–2.58 (4H, m), 1.85–2.14 (3H, m), 1.06–1.78 (29H, m), 0.81–1.00 (21H, m).

EXAMPLE 4

4-i)

To a mixed solvent of dioxane (162 ml), water (83 ml) and 1M aqueous sodium carbonate (83 ml) was added 5-aminovaleric acid (10 g). To the solution was added under ice-cooling di-t-butyl dicarbonate (19.9 g). After stirring at room temperature overnight, the mixture was concentrated under reduced pressure to about 100 ml. After being adjusted to pH 3 with 10% aqueous citric acid under ice-cooling, the mixture was extracted with ethyl acetate. The organic layer was washed with water and dried over sodium sulfate. After the solvent was removed in vacuo, the residue was recrystallized from hexane-ethyl acetate to afford 17 g of N-Boc-5-aminovaleric acid.

$^1$H-NMR (δ ppm, CDCl$_3$): 5.78 (1H, br s), 4.61 (1H, br s), 3.05–3.20 (2H, m), 2.38 (2H, t, J=7.3 Hz), 1.60–1.70 (2H, m), 1.44 (9H, s), 1.35–1.60 (2H, m).

4-ii)

To a solution of N-Boc-5-aminovaleric acid (3 g) thus obtained, dimethylaminopyridine (0.15 g) and benzyl alcohol (1.36 ml) in dichloromethane (50 ml) was added WSCI (2.89 g) under ice-cooling. The solution was stirred under ice-cooling for 2 hours and then at room temperature overnight. After the solvent was removed in vacuo, to the residue were added ethyl acetate and water. The separated ethyl acetate layer was washed twice with 5% aqueous sodium hydrogencarbonate and twice with water and then dried over anhydrous sodium sulfate. After the solvent was removed in vacuo, the residue was purified by a silica gel column chromatography to afford 4 g of benzyl N-Boc-5-aminovalerate.

¹H-NMR (δ ppm, CDCl₃): 7.27–7.37 (5H, m), 5.11 (2H, s), 4.53 (1H, br s), 3.05–3.15 (2H, m), 2.38 (2H, t, J=7.3 Hz), 1.55–1.70 (2H, m), 1.44 (9H, s), 1.35–1.60 (2H, m).

4-iii)

A mixture of benzyl N-Boc-5-aminovalerate (4 g) thus obtained in TFA (50 ml) was stirred at room temperature for 20 minutes. After the TFA was removed in vacuo, ethyl acetate and saturated aqueous sodium hydrogencarbonate were added. The separated ethyl acetate layer was dried over anhydrous sodium sulfate. The solvent was removed in vacuo to afford 2.7 g of benzyl 5-aminovalerate.

¹H-NMR (δ ppm, CDCl₃): 7.80 (2H, br s), 7.25–7.38 (5H, m), 5.07 (2H, s), 2.85–2.95 (2H, m), 2.35–2.45 (2H, m), 1.60–1.70 (4H, m).

4-iv)

To a solution of benzyl 5-aminovalerate (2.04 g) thus obtained, Fmoc-aspartic acid β-t-butyl ester (2.03 g) and HOBt.monohydrate (0.83 g) in dichloromethane (30 ml) was added WSCI (1.04 g) under ice-cooling. The solution was stirred under ice cooling for 2 hours and then at room temperature overnight. After the solvent was removed in vacuo, the residue was dissolved in ethyl acetate, and the solution was washed successively with 10% aqueous citric acid, water, 5% aqueous sodium hydrogencarbonate and water and then dried over anhydrous sodium sulfate. After the solvent was removed in vacuo, the residue was purified by a silica gel column chromatography to afford 2.41 g of Intermediate 17.

¹H-NMR (δ ppm, CDCl₃): 7.76 (2H, d, J=7.8 Hz), 7.58 (2H, d, J=7.3 Hz), 7.23–7.46 (6H, m), 6.52 (1H, br s), 5.94 (1H, d, J=8.0 Hz), 5.09 (2H, s), 4.36–4.55 (3H, m), 4.22 (1H, t, J=6.8 Hz), 3.15–3.29 (2H, m), 2.90 (1H, d, J=17 Hz), 2.59 (1H, dd, J=6.4, 17 Hz), 2.37 (2H, t, J=7.3 Hz), 1.58–1.82 (2H, m), 1.44 (9H, s), 1.35–1.58 (2H, m).

4-v)

A suspension of Intermediate 17 (Fmoc-Asp(OtBu)—NH—(CH₂)₄—CO₂Bzl) (0.69 g) and 5% palladium-carbon (70 mg) in methanol (20 ml) was treated under hydrogen atmosphere (2 kg/cm²) at room temperature for 5 hours. The palladium-carbon was filtered off, the methanol was removed in vacuo and the resulting crude product was purified by a silica gel column chromatography and then further solidified with hexane-diethyl ether to afford 0.26 g of Intermediate 18.

¹H-NMR (δ ppm, CDCl₃): 7.76 (2H, d, J=7.3 Hz), 7.58 (2H, d, J=7.3 Hz), 7.40 (2H, t, J=7.3 Hz), 7.31 (2H, t, J=7.6 Hz), 6.62 (1H, t, J=5.9 Hz), 6.03 (1H, d, J=8.8 Hz), 4.49 (1H, br s), 4.43 (2H, d, J=6.8 Hz), 4.21 (1H, t, J=7.1 Hz), 3.26 (2H, q, J=6.3 Hz), 2.89 (1H, dd, J=3.9, 18 Hz), 2.61 (1H, dd, J=6.8, 17 Hz), 2.35 (2H, t, J=7.1 Hz), 1.60–1.70 (2H, m), 1.50–1.59 (2H, m), 1.44 (9H, s).

4-vi)

To a solution of Intermediate 2 (benzyl 3-hydroxymyristate) (0.16 g), Intermediate 18 (0.25 g) and dimethylaminopyridine (4 mg) in dichloromethane (5 ml) was added DCC (0.15 g) under ice-cooling. The solution was stirred under ice-cooling for 2 hours and then at room temperature for 4 days. After the precipitate was filtered off, the dichloromethane was removed in vacuo. To the residue were added ethyl acetate and 10% aqueous citric acid. The organic layer thus obtained was washed successively with water, 5% aqueous sodium hydrogencarbonate and water and then dried over anhydrous sodium sulfate. After the solvent was removed in vacuo, the residue was purified by a silica gel column chromatography to afford 0.36 g of Compound 12.

¹H-NMR (δ ppm, CDCl₃): 7.76 (2H, d, J=7.3 Hz), 7.58 (2H, d, J=7.3 Hz), 7.40 (2H, t, J=7.3 Hz), 7.28–7.38 (7H, m), 6.53 (1H, br s), 5.95 (1H, d, J=8.3 Hz), 5.22 (1H, qui., J=6.3 Hz), 5.10 (2H, s), 4.47 (1H, br s), 4.43 (2H, d, J=6.8 Hz), 4.22 (1H, t, J=7.1 Hz), 3.22 (2H, q, J=6.5 Hz), 2.90 (1H, dd, J=4.2, 16 Hz), 2.53–2.65 (3H, m), 2.21 (2H, dt, J=2.9, 7.3 Hz), 1.44 (9H, s), 1.41–1.65 (4H, m), 1.04–1.41 (20H, m), 0.88 (3H, t, J=6.8 Hz).

4-vii)

To a solution of Compound 12 (0.36 g) in DMF (5 ml) was added at room temperature diethylamine (0.5 ml). The solution was stirred at room temperature for 2 hours and then concentrated under reduced pressure. To a solution of the amine derivative thus obtained, Fmoc-L-valine (0.18 g) and HOBt-monohydrate (0.08 g) in dichloromethane (10 ml) was added WSCI (0.10 g) under ice-cooling. The solution was stirred under ice-cooling for 2 hours and then at room temperature overnight. After the dichloromethane was removed in vacuo, to the residue were added chloroform and 10% aqueous citric acid. The separated chloroform layer was washed successively with water, 5% aqueous sodium hydrogencarbonate and water and then dried over anhydrous sodium sulfate. After the chloroform was removed in vacuo, the residue was purified by a silica gel column chromatography to afford 0.40 g of Compound 13.

¹H-NMR (δ ppm, CDCl₃) : 7.77 (2H, d, J=7.3 Hz), 7.60 (2H, dd, J=3.7, 6.8 Hz), 7.40 (2H, t, J=7.1 Hz), 7.24–7.36 (8H, m), 6.74 (1H, br s), 5.30 (1H, d, J=7.3 Hz), 5.21 (1H, qui., J=6.3 Hz), 5.10 (2H, s), 4.66–4.74 (1H, m), 4.37–4.48 (2H, m), 4.23 (1H, t, J=6.8 Hz), 4.01 (1H, br s), 3.10–3.26 (2H, m), 2.86–2.97 (1H, m), 2.51–2.65 (3H, m), 2.17 (2H, dt, J=3.1, 7.3 Hz), 2.14–2.20 (1H, m), 1.35–1.63 (4H, m), 1.41 (9H, s), 1.04–1.35 (20H, m), 0.98 (3H, d, J=6.8 Hz), 0.93 (3H, d, J=6.3 Hz), 0.88 (3H, t, J=6.8 Hz).

4-viii)

To a solution of Compound 13 (0.40 g) in methanol (20 ml) was added 5% palladium-carbon (40 mg) and the mixture was stirred under hydrogen atmosphere at room temperature for 10 hours. The palladium-carbon was filtered off, the methanol was removed in vacuo and the resulting crude product was purified by a silica gel column chromatography to afford 0.34 g of Compound 14.

¹H-NMR (δ ppm, CDCl₃): 7.76 (2H, d, J=7.3 Hz), 7.54–7.67 (3H, m), 7.40 (2H, d, J=7.6 Hz), 7.31 (2H, t, J=7.6 Hz), 6.87–6.98 (1H, m), 5.73 (1H, br s), 5.19–5.30 (1H, m), 4.71–4.80 (1H, m), 4.33–4.45 (2H, m), 4.19–4.25 (1H, m), 4.03–4.11 (1H, m), 3.06–3.34 (2H, m), 2.75–2.87 (1H, m), 2.49–2.72 (3H, m), 2.10–2.37 (3H, m), 1.40–1.71 (4H, m), 1.40 (9H, s), 1.16–1.35 (20H, m), 0.98 (3H, d, J=6.8 Hz), 0.94 (3H, d, J=6.8 Hz), 0.88 (3H, t, J=6.8 Hz).

4-ix)

To a solution of Compound 14 (0.34 g), Gln(Mbh)-Leu-OtBu (0.22 g) and HOBt-monohydrate (0.06 g) in DMF (10 ml) was added WSCI (0.08 g) under ice-cooling. The solution was stirred under ice-cooling for 2 hours and then at room temperature overnight. After the DMF was removed in vacuo, to the residue were added chloroform and 10% aqueous citric acid. The separated chloroform layer was washed successively with water, 5% aqueous sodium hydrogencarbonate and water and then dried over anhydrous sodium sulfate. After the chloroform was removed in vacuo, the residue was purified by a silica gel column chromatography to afford 0.47 g of Compound 15.

¹H-NMR (δ ppm, CDCl₃): 7.76 (2H, d, J=7.8 Hz), 7.59 (2H, d, J=7.3 Hz), 7.40 (2H, t, J=7.6 Hz), 7.30 (2H, dt, J=1.1, 7.6 Hz), 7.28–7.47 (3H, m), 7.14 (2H, dd, J=2.4, 8.8 Hz), 7.16 (2H, t, J=7.6 Hz), 7.05–7.21 (1H, m), 6.85–7.04 (2H, m), 6.82 (4H, dd, J=2.0, 8.8 Hz), 6.20 (1H, d, J=7.8 Hz), 5.52, 5.47 (1H, 2d, J=8.3 Hz), 5.12–5.22 (1H, m), 4.66–4.77 (1H, m), 4.30–4.49 (4H, m), 4.21 (1H, dt, J=2.9, 6.8 Hz), 3.95–4.05 (1H, m), 3.76 (6H, 2s), 3.06–3.27 (2H, m), 2.72–2.83 (1H, m), 2.51–2.65 (1H, m), 2.32–2.48 (4H, m), 1.99–2.27 (4H, m), 1.43 (9H, s), 1.39 (9H, s), 1.35–1.66 (7H, m), 1.17–1.34 (20H, m), 0.80–0.99 (15H, m).

4-x)

Compound 15 (0.47 g) was dissolved in TFA (5 ml). The solution was stirred at room temperature for 2 hours and then concentrated under reduced pressure. After chloroform was added to the residue, pH of the mixture was adjusted to about 7 with a saturated aqueous sodium hydrogencarbonate. The solid thus separated was recovered by filtration, washed with chloroform and then dried to afford. 0.29 g of Compound 16.

$^1$H-NMR ($\delta$ ppm, DMSO-d6): 8.10–8.30 (1H, m), 7.97–8.07 (1H, m), 7.86 (2H, d, J=7.8 Hz), 7.68–7.89 (3H, m), 7.40 (2H, t, J=7.3 Hz), 7.31 (2H, t, J=7.3 Hz), 7.28–7.43 (1H, m), 7.15–7.24 (1H, m), 6.78–6.84 (1H, m), 6.62 (1H, br s), 5.04–5.12 (1H, m), 4.48–4.56 (1H, m), 4.11–4.34 (5H, m), 3.82–3.88 (1H, m), 3.66–3.75 (1H, m), 2.95–2.98 (2H, m), 2.31–2.68 (4H, m), 2.15–2.23 (2H, m), 1.83–2.12 (4H, m), 1.59–1.76 (2H, m), 1.33–1.57 (7H, m), 1.16–1.30 (20H, m), 0.79–0.92 (15H, m).

EXAMPLE 5

5-i)

To a solution of Intermediate 2 (3.18 g), Fmoc-L-isoleucine (3.70 g) and dimethylaminopyridine (0.10 g) in dichloromethane (250 ml) was added DCC (3.14 g) under ice-cooling. The mixture was stirred under ice-cooling for one hour and then at room temperature overnight. After the precipitate was filtered off, the dichloromethane was removed in vacuo. To the residue was added ethyl acetate (30 ml). Insolubles were filtered off and then the ethyl acetate was removed in vacuo. The residue was purified by a silica gel column chromatography to afford 7.14 g of Intermediate 19.

$^1$H-NMR ($\delta$ ppm, CDCl$_3$) 7.29–7.77 (13H, m), 5.27–5.33 (2H, m), 5.11 (2H, s), 4.29–4.34 (3H, m), 4.23 (1H, t, J=6.8 Hz), 2.57–2.72 (2H, m), 1.07–1.90 (23H, m), 0.86–0.95 (9H, m).

5-ii)

To a solution of Intermediate 19 (7.14 g) in DMF (70 ml) was added diethylamine (7 ml) and the mixture was stirred at room temperature for 5 hours. After the solvent was removed in vacuo, the residue was purified by a silica gel column chromatography to afford 4.33 g of Intermediate 20.

$^1$H-NMR ($\delta$ ppm, CDCl$_3$) 7.33–7.36 (5H, m), 5.24–5.31 (1H, m), 5.11 (2H, s), 3.19 (1H, d, J=4.9 Hz), 2.57–2.66 (2H, m), 1.05–1.75 (25H, m), 0.86–0.94 (9H, m).

5-iii)

To a solution of Fmoc-L-aspartic acid t-butyl ester (9.05 g), D-leucine benzyl ester (4.43 g) and HOBt-monohydrate (3.37 g) in dichloromethane (80 ml) was added WSCI (4.22 g) under ice-cooling and the mixture was stirred at that temperature for 2 hours and then at room temperature overnight. After the dichloromethane was removed in vacuo, to the residue was added ethyl acetate and the mixture was washed successively with 10% aqueous citric acid, water, 5% aqueous sodium hydrogencarbonate and water and then dried over anhydrous sodium sulfate. After the solvent was removed in vacuo, the crude product thus obtained was purified by crystallization from hexane-ethyl acetate to afford 8.36 g of Intermediate 21.

$^1$H-NMR ($\delta$ ppm, CDCl$_3$) 7.77 (2H, d, J=7.3 Hz), 7.59 (2H, d, J=7.8 Hz), 7.40 (2H, t, J=7.3 Hz), 7.28–7.37 (7H, m), 6.94 (1H, d, J=7.8 Hz), 5.96 (1H, d, J=7.8 Hz), 5.17 (1H, d, J=12 Hz), 5.13 (1H, d, J=12 Hz), 4.53–4.67 (2H, m), 4.39 (2H, d, J=6.8 Hz), 4.23 (1H, t, J=7.1 Hz), 2.89 (1H, dd, J=3.2, 17 Hz), 2.62 (1H, dd, J=6.8, 17 Hz), 1.51–1.70 (3H, m), 1.44 (9H, s), 0.90 (3H, d, J=2.4 Hz), 0.88 (3H, d, J=2.4 Hz).

5-iv)

To a solution of Intermediate 21 (6.15 g) in DMF (100 ml) was added diethylamine (10 ml) and the mixture was stirred at room temperature for 3 hours. The solvent was removed in vacuo to afford 3.93 g of Intermediate 22.

$^1$H-NMR ($\delta$ ppm, d$_6$-DMSO) 7.86 (1H, d, J=7.8 Hz), 7.68–7.75 (3H, m), 7.49 (1H, d, J=8.3 Hz), 7.38–7.42 (2H, m), 7.29–7.33 (2H, m), 4.18–4.41 (5H, m), 2.64–2.69 (1H, m), 2.43–2.49 (1H, m), 1.69–1.73 (1H, m), 1.42–1.48 (1H, m), 1.37 (9H, s), 0.86 (9H, s).

5-v)

To a solution of Intermediate 22 (3.93 g), Fmoc-L-valine (3.39 g) and HOBt-monohydrate (1.53 g) in DMF (70 ml) was added WSCI (1.92 g) under ice-cooling and the mixture was stirred at that temperature for 2 hours and then at room temperature overnight. After the DMF was removed in vacuo, to the residue was added chloroform and the mixture was washed successively with 10% aqueous citric acid, water, 5% aqueous sodium hydrogencarbonate and water and then dried over anhydrous sodium sulfate. After the solvent was removed in vacuo, the crude product thus obtained was solidified from chloroform-diethyl ether to afford 6.19 g of Intermediate 23.

$^1$H-NMR ($\delta$ ppm, CDCl$_3$) 7.77 (2H, d, J=7.3 Hz), 7.60 (2H, d, J=8.3 Hz), 7.40 (2H, dt, J=3.4, 7.3 Hz), 7.27–7.37 (7H, m), 7.22 (1H, d, J=7.8 Hz), 7.08 (1H, d, J=7.3 Hz), 5.29 (1H, d, J=6.8 Hz), 5.09 (2H, s), 4.79–4.86 (1H, m), 4.56–4.63 (1H, m), 4.41 (2H, d, J=7.3 Hz), 4.23 (1H, t, J=6.8 Hz), 4.01 (1H, t, J=6.3 Hz), 2.90 (1H, dd, J=4.4, 17 Hz), 2.58 (1H, dd, J=6.5, 17 Hz), 2.10–2.20 (1H, m), 1.56–1.68 (3H, m), 1.42 (9H, s), 0.98 (3H, d, J=6.8 Hz), 0.93 (3H, d, J=6.8 Hz), 0.85–0.91 (6H, m).

5-vi)

To a solution of 5-amino-3-pentenoic acid (0.57 g) in dioxane (20 ml) were added in turn under ice-cooling conc. sulfuric acid (0.6 ml) and a solution of isobutylene (1.5 ml) in dichloromethane (2.5 ml). The reaction vessel was tightly sealed and the mixture was stirred at room temperature for 14 hours. The reaction vessel was opened after ice-cooling, to the reaction solution was added a solution of sodium hydroxide (1.7 g) in water (30 ml) and extracted with diethyl ether and chloroform. The organic layer was separated and dried over anhydrous sodium sulfate. The solvent was removed in vacuo to afford 0.14 g of Intermediate 25.

$^1$H-NMR ($\delta$ ppm, CDCl$_3$) 5.68–5.66 (2H, m), 3.32 (2H, br s), 2.97–2.99 (2H, m), 1.87 (2H, br s), 1.45 (9H, s).

5-vii)

A solution of Intermediate 23 (5.12 g) in DMF (15 ml) was diluted with methanol (250 ml). To the solution was added 10% palladium-carbon (0.96 g) and the resulting suspension was stirred under hydrogen atmosphere (one atmospheric pressure) at room temperature for 2 hours. The palladium-carbon was filtered off and the solvent was removed in vacuo from the filtrate to afford 4.87 g of Intermediate 24. A solution of 3.84 g of Intermediate 24 in DMF (10 ml) was diluted with dichloromethane (20 ml). To the solution were added Intermediate 20 (2.68 g) and HOBt-monohydrate (1.04 g) at room temperature and then the mixture was ice-cooled and WSCL (1.77 g) was added. The mixture was stirred under ice-cooling for 2 hours and then at room temperature overnight. The reaction solution was diluted with chloroform (50 ml), washed with saturated aqueous sodium chloride and dried over anhydrous sodium sulfate. After the solvent was removed in vacuo, the residue was purified by a silica gel column chromatography to afford 4.88 g of Compound 17.

$^1$H-NMR (δ ppm, CDCl$_3$) 7.27–7.76 (13H, m), 6.99 (1H, br), 6.91 (2H, br), 6.83 (1H, br), 5.57 (1H, br), 5.19–5.24 (1H, m), 5.02–5.10 (2H, m), 3.95–4.85 (7H, m), 2.46–2.86 (4H, m), 1.08–2.11 (36H, m), 0.85–0.95 (21H, m).

5-viii)

To a solution of Compound 17 (4.88 g) in methanol (350 ml) was added 10% palladium-carbon (0.98 g) and the resulting suspension was stirred under hydrogen atmosphere at room temperature for 2 hours. After the palladium-carbon was filtered off and the solvent was removed in vacuo from the filtrate, the residue was purified by a silica gel column chromatography to afford 3.58 g of Compound 18.

$^1$H-NMR (δ ppm, d$_6$-DMSO) 12.25 (1H, br), 7.28–8.27 (12H, m), 5.04–5.09 (1H, m), 4.56–4.58 (1H, m), 4.14–4.31 (5H, m), 3.81–3.84 (1H, m), 2.38–2.70 (4H, m), 1.87–2.01 (1H, m), 1.74–1.78 (1H, m), 1.09–1.53 (34H, m), 0.78–0.87 (21H, m).

5-ix)

To a solution of Intermediate 25 (0.19 g), Compound 18 (0.52 g) and HOBt-monohydrate (0.19 g) in dichloromethane (20 ml) was added WSCI (0.32 g) at room temperature and the mixture was stirred for 22 hours. After the dichloromethane was removed in vacuo, the residue was purified by a silica gel column chromatography to afford 0.56 g of Compound 19.

$^1$H-NMR (δ ppm, d$_6$-DMSO) 7.76 (2H, d, J=7.3 Hz), 7.59–7.64 (3H, m), 6.90–7.42 (8H, m), 6.20–6.27 (1H, m), 5.64–5.72 (1H, m), 5.50–5.54 (1H, m), 5.14–5.21 (1H, m), 4.81–4.88 (1H, m), 4.21–4.51 (6H, m), 3.71–3.98 (4H, m), 2.73–2.99 (2H, m), 2.15–2.51 (2H, m), 1.08–1.92 (45H, m), 0.86–0.99 (21H, m).

5-x)

A solution of Compound 19 (0.56 g) in TFA (3 ml) was stirred at room temperature for 90 minutes and diluted with chloroform (30 ml) and then washed with water. The organic layer was separated and the solvent was removed in vacuo. To the residue (0.33 g) were added diethyl ether and hexane and the precipitate thus separated out was recovered by filtration and dried under reduced pressure to afford 0.33 g of Compound 20.

$^1$H-NMR (δ ppm, d$_6$-DMSO) 12.18 (1H, br), 8.27 (1H, br), 7.68–8.00 (7H, m), 7.29–7.42 (6H, m), 5.44–5.65 (2H, m), 5.08–5.15 (1H, m), 4.54–4.56 (1H, m), 4.12–4.31 (5H, m), 3.83–3.89 (1H, m), 3.57–3.69 (2H, m), 2.96 (2H, d, J=6.6 Hz), 2.28–2.67 (4H, m), 1.01–2.00 (27H, m), 0.82–0.87 (21H, m).

EXAMPLE 6

6-i)

To a solution of dichloromethane (5 ml) containing oxalyl chloride (0.40 ml) was added dropwise at −60° C. a solution of dichloromethane (3 ml) containing DMSO (0.70 ml). The mixture was stirred for 10 minutes, a solution of dichloromethane (15 ml) containing Fmoc-L-valinol (1.00 g) was added dropwise thereto over 15 minutes and the mixture was stirred at −60° C. for 30 minutes. To the reaction solution was added isopropylethylamine (2.6 ml) and the mixture was stirred at room temperature for 30 minutes and the saturated aqueous sodium chloride was added. The dichloromethane layer was separated and dried over anhydrous sodium sulfate. After the dichloromethane was removed in vacuo, the residue was purified by a silica gel column chromatography to afford 1.25 g of Intermediate 26.

$^1$H-NMR (δ ppm, CDCl$_3$) 9.66 (1H, s), 7.76 (2H, d, J=7.3 Hz), 7.60 (2H, d, J=7.3 Hz), 7.41 (2H, t, J=7.3 Hz), 7.30–7.34 (2H, m), 5.36 (1H, d, J=7.8 Hz), 4.17–4.62 (4H, m), 2.30–2.35 (1H, m), 1.04 (3H, d, J=6.8 Hz), 0.96 (3H, d, J=7.3 Hz).

6-ii)

To a solution of Intermediate 26 (1.25 g) and L-aspartic acid a-benzyl P-t-butyl ester (0.86 g) in 1,2-dichloroethane (15 ml) was added sodium triacetoxyborohydride (0.89 g) while stirring at room temperature and the mixture was stirred for 13 hours. To the reaction solution was added 5% aqueous sodium hydrogencarbonate and the separated organic layer was washed with saturated aqueous sodium chloride and dried over anhydrous sodium sulfate. After the 1,2-dichloroethane was removed in vacuo, the residue was purified by a silica gel column chromatography to afford 1.55 g of Intermediate 27.

$^1$H-NMR (δ ppm, CDCl$_3$) 7.75 (2H, d, J=7.3 Hz), 7.59–7.62 (2H, m), 7.27–7.52 (10H, m), 5.17 (1H, d, J=12 Hz), 5.13 (1H, d, J=12 Hz), 4.84 (1H, d, J=7.8 Hz), 4.35–4.45 (2H, m), 4.22 (1H, t, J=6.8 Hz), 3.65 (1H, br), 3.46 (1H, br), 2.51–2.76 (3H, m), 1.87 (1H, br), 1.40 (9H, s), 0.84–0.88 (6H, m).

6-iii)

To a solution of Intermediate 27 (0.81 g) in methanol (50 ml) was added 5% palladium-carbon (0.20 g) and the resulting suspension was stirred under hydrogen atmosphere at room temperature for 30 minutes. The palladium-carbon was filtered off and the methanol was removed in vacuo to afford 0.59 g of Intermediate 28.

$^1$H-NMR (δ ppm, d$_6$-DMSO) 7.86 (2H, d, J=7.3 Hz), 7.67–7.71 (2H, m), 7.30–7.42 (4H, m), 7.05 (1H, d, J=8.3 Hz), 4.21–4.36 (3H, m), 3.44 (2H, brs), 2.44–2.78 (4H, m), 1.78 (1H, br), 1.39 (9H, s), 0.80–0.84 (6H, m).

6-iv)

To a solution of (R)-3-hydroxymyristic acid (2.50 g) and triethylamine (1.43 ml) in DMF (25 ml) was added phenacyl bromide (2.04 g) at room temperature and the mixture was stirred overnight. After the solvent was removed, ethyl acetate was added and washed three times with water. After drying over anhydrous sodium sulfate, the ethyl acetate was removed in vacuo, and the residue was purified by a silica gel column chromatography to afford 3.53 g of Intermediate 29.

$^1$H-NMR (δ ppm, CDCl$_3$) 7.92 (2H, d, J=6.8 Hz), 7.63 (1H, d, J=7.3 Hz), 7.50 (2H, d, J=7.6 Hz), 5.48 (1H, d, J=17 Hz), 5.37 (1H, d, J=17 Hz), 4.09–4.18 (1H, m), 3.41 (1H, br s), 2.70 (1H, dd, J=2.9, 15 Hz), 2.57 (1H, dd, J=9.3, 15 Hz), 1.19–1.67 (20H, m), 0.88 (3H, t, J=6.8 Hz).

6-v)

To a solution of 5-amino-3-pentenoic acid (1.00 g) in 10% aqueous sodium carbonate (20 ml) and dioxane (10 ml) was added under ice-cooling a solution of Fmoc-Cl (2.20 g) in dioxane (10 ml) and the mixture was stirred overnight. The reaction solution was diluted with ethyl acetate and extracted three times with 10% aqueous sodium carbonate. The aqueous layer was acidified with 1N hydrochloric acid and extracted with ethyl acetate. The organic layer was washed successively with water and saturated aqueous sodium chloride and dried over anhydrous sodium sulfate. The ethyl acetate was removed in vacuo to afford 2.44 g of Intermediate 30.

$^1$H-NMR (δ ppm, CDCl$_3$) 7.75–7.76 (2H, m), 7.57–7.59 (2H, m), 7.37–7.41 (2H, m), 7.28–7.32 (2H, m), 5.50–5.70 (2H, m), 4.88 (1H, m), 4.40–4.43 (2H, m), 4.20–4.30 (1H, m), 3.60–3.82 (2H, m), 3.00–3.12 (2H, m).

6-vi)

To a solution of Intermediate 29 (0.86 g), Intermediate 30 (0.93 g) and DMAP (61 mg) in dichloromethane (30 ml) was added DCC (0.77 g) under ice-cooling. The mixture was stirred under ice-cooling for 2 hours and then at room temperature overnight. After the precipitate was filtered off, the dichloromethane was removed in vacuo. To the residue was added ethyl acetate (30 ml). The mixture was washed successively with 10% aqueous citric acid, water, 5% aqueous sodium hydrogencarbonate and water and then dried over anhydrous sodium sulfate. After the solvent was removed in vacuo, the resulting crude product was purified by a silica gel chromatography to afford 1.54 g of Intermediate 31.

$^1$H-NMR (δ ppm, CDCl$_3$) 7.88 (2H, d, J=6.8 Hz), 7.75 (2H, d, J=7.8 Hz), 7.58 (2H, d, J=7.3 Hz), 7.58 (1H, t, J=7.6 Hz), 7.45 (2H, t, J=7.6 Hz), 7.39 (2H, t, J=7.6 Hz), 7.30 (2H, t, J=7.3 Hz), 5.69–5.80 (1H, m), 5.57–5.68 (1H, m), 5.27–38 (3H, m), 4.99 (1H, br s), 4.36 (2H, d, J=6.8 Hz), 4.19 (1H, t, J=6.6 Hz), 3.81 (2H, br s), 3.05–3.17 (2H, m), 2.77 (1H, dd, J=3.4 Hz), 2.75 (1H, d, J=1.5 Hz), 1.53–1.76 (2H, m), 1.18–1.41 (18H, m), 0.88 (3H, t, J=6.8 Hz).

6-vii)

To a solution of Intermediate 31 (0.33 g) in DMF (5 ml) was added diethylamine (0.4 ml) and the mixture was stirred at room temperature for 90 minutes. The reaction solution was concentrated under reduced pressure to afford Intermediate 32. To a solution of Intermediate 32 (0.31 g) in DMF (30 ml) were added Intermediate 28 (0.25 g) and HOBt-monohydrate (90 mg) while stirring at room temperature. The solution was ice-cooled, WSCI (0.14 g) was added and the mixture was stirred at room temperature overnight. After insolubles were filtered off, the solvent was removed in vacuo, and the residue was purified by a silica gel column chromatography to afford 0.10 g of Compound 21.

$^1$H-NMR (δ ppm, CDCl$_3$) 7.87 (2H, d, J=7.3 Hz), 7.75 (2H, d, J=7.3 Hz), 7.28–7.61 (11H, m), 5.66–5.74 (1H, m), 5.52–5.59 (1H, m), 5.25–5.31 (3H, m), 4.86 (1H, d, J=9.8 Hz), 4.47–4.51 (1H, m), 4.33–4.37 (1H, m), 4.19–4.22 (1H, m), 3.76–3.88 (2H, m), 3.57 (1H, br), 3.34–3.37 (1H, m), 3.00–3.11 (2H, m), 2.46–2.77 (5H, m), 1.74–1.79 (1H, m), 1.65 (2H, br s), 1.41 (9H, s), 1.24–1.28 (18H, m), 0.86–0.92 (9H, m).

6-viii)

To a solution of Compound 21 (77 mg) in acetic acid (3 ml) was added powdery zinc (150 mg) and the mixture was stirred at 50° C. for 4 hours. After insolubles were filtered off, the solvent was removed in vacuo, and the residue was purified by a silica gel column chromatography to afford 41 mg of Compound 22.

$^1$H-NMR (δ ppm, CDCl$_3$) 7.75 (2H, d, J=7.3 Hz), 7.54–7.61 (2H, m), 7.29–7.41 (5H, m), 6.46 (1H, d, J=8.8 Hz), 5.53–5.67 (2H, m), 5.09–5.20 (2H, m), 4.32–4.55 (3H, m), 3.81 (2H, br s), 3.51–3.60 (2H, m), 2.31–3.02 (7H, m), 1.03–1.81 (30H, m), 0.78–0.94 (9H, m).

6-ix)

A solution of Compound 22 (41 mg) in TFA (1 ml) was stirred at room temperature for one hour. After the TFA was removed in vacuo, the residue was purified by a silica gel column chromatography to afford 31 mg of Compound 23.

$^1$H-NMR (δ ppm, CD$_3$OD) 7.78 (2H, d, J=7.3 Hz), 7.64–7.67 (2H, m), 7.28–7.40 (4H, m), 5.55 (2H, br s), 5.36 (1H, br s), 4.50–4.54 (1H, m), 4.20–4.34 (2H, m), 3.90–3.95 (1H, m), 3.56 (1H, br s), 3.42 (1H, br s), 2.92–3.05 (2H, m), 2.39–2.67 (7H, m), 1.71 (1H, br s), 1.26–1.29 (20H, m), 0.87–0.94 (9H, m).

TEST EXAMPLE

It will be shown below that the depsipeptides of the invention may influence upon the productivity of apolipoprotein E in Hep G2 cells, together with the test procedure as used.

First, Hep G2 cells were suspended at 1×10$^5$ cells/ml in Dulbecco's modified Eagle medium (manufactured by Nissui Seiyaku Co., Ltd.; hereinafter referred to as "D-MEM medium") containing 10% fetal bovine serum and 1 ml portions of the suspension were poured into a 24-well tissue culture plate. Cultivation was carried out at 37° C. under atmosphere of a mixed gas composed of 5% carbon dioxide and 95% air. After 3 days, the medium was removed by means of a pipette, 1 ml of a fresh D-MEM medium was added and then 10 μl aliquot of methanolic solutions of the present Compounds 5, 7, 11, 16, 20 and 23, was further added at the concentration as shown in Table 1. After 18 hours, the medium was again replaced (D-MEM medium), 10 μl each of methanolic solutions of the depsipeptides was added and cultivation was further conducted at 37° C. for 8 hours. The supernatant thus obtained was used as a sample solution. The apolipoprotein E produced in the cultured broth was assayed by means of an enzyme immunoassay method.

And, the compositions of the buffers applied in the enzyme immunoassay are summarized below. In this connection, PBS represents phosphate-buffered saline, PBS-T represents phosphate-buffered saline having incorporated Tween 20 and a blocking solution is the phosphate buffer containing the immunosuppressive agent "Block Ace" which is derived from lactoprotein and manufactured by Dainippon Pharmaceutical Co., Ltd.

| PBS (pH 7.2) | |
|---|---|
| KH$_2$PO$_4$ | 0.2 g |
| Na$_2$HPO$_4$.12H$_2$O | 2.9 g |
| NaCl | 8.0 g |
| KCl | 0.2 g |
| Distilled water | q.s. |
| Total | 1000 ml |
| PBS-T (pH 7.2) | |
| KH$_2$PO$_4$ | 0.2 g |
| Na$_2$HPO$_4$.12H$_2$O | 2.9 g |
| NaCl | 8.0 g |
| KCl | 0.2 g |
| Tween 20 | 0.5 g |
| Distilled water | q.s. |
| Total | 1000 ml |
| Blocking solution (pH 7.2) | |
| Block Ace | 250 ml |
| KH$_2$PO$_4$ | 0.2 g |
| Na$_2$HPO$_4$.12H$_2$O | 2.9 g |
| NaCl | 8.0 g |
| KCl | 0.2 g |

-continued

| | |
|---|---|
| Distilled water | q.s. |
| Total | 1000 ml |

1) Determination of apolipoprotein E

The mouse antihuman apolipoprotein E monoclonal antibody (manufactured by BYOSIS, S. A., France) was dissolved in a 0.05M aqueous sodium hydrogencarbonate solution (pH 9.5) at a concentration of 5 μg/ml. 50 μl of the solution was poured into Nunc immunoplates which were then allowed to stand at 4° C. for 16 hours. They were washed three times with 300 μl of PBS, 300 μl of the blocking solution was added and the mixture was allowed to stand at 37° C. for 2 hours and then at 4° C. for 16 hours.

It was again washed three times with 300 μl of PBS, 50 μl of the above sample solution (the medium for Hep G2 cells) was added and the mixture was allowed to stand at room temperature for 2 hours. After washing three times with 300 μl of PBS-T, 50 μl of a 3000-fold diluted solution (10% aqueous Block Ace solution) of goat anti-apolipoprotein E polyclonal antibody (manufactured by Chemicon Co., Ltd., U.S.A.) was added and the mixture was allowed to stand at room temperature for 2 hours. The mixture was washed three times with 300 μl of PBS-T, a 5000-fold diluted solution (a 10% aqueous solution of Block Ace) of a peroxidase-labeled anti-goat TgG polyclonal antibody (manufactured by Bindingsite Co., Ltd., U.K.) was added and the mixture was allowed to stand at room temperature for 2 hours. After washing five times with 300 μl of PBS-T, 100 μl of a coloring solution (Composition: 0.1M potassium citrate (pH 4.5) 1 ml, 30% aqueous hydrogen peroxide 0.4 μl, orthophenylenediamine 1 mg) was added and the mixture was allowed to stand as such for 2 minutes. The reaction was quenched by the addition of 100 μl of 2N sulfuric acid and absorbance was measured at 490 nm using absorbance at 650 nm as a control. An amount of apolipoprotein E in the present depsipeptide was determined upon the calibration curve drawn up when a commercially available apolipoprotein E (Chemicon Co., Ltd., U.S.A.) was used as a standard.

In the Test Example, the same procedure as described above was carried out except that methanol alone was added instead of the methanolic solution of the present depsipeptide and an apolipoprotein E amount was measured as a control. A relative apolipoprotein E amount by the present depsipeptide was represented in terms of a relative value (%) when the control was defined as 100.

As shown in Table 1, it was proved that the depsipeptides of the invention have a potent promoting activity on the productivity of apolipoprotein E at 1–5 μM.

TABLE 1

| Compound | Conc. (μM) | Relative amount of apolipoprotein E (%) |
|---|---|---|
| 5 | 5 | 144 |
| 7 | 5 | 151 |
| 11 | 1 | 333 |
| 16 | 1 | 165 |
| 20 | 1 | 327 |
| 23 | 1 | 161 |
| 23 | 5 | 275 |
| Control | 0 | 100 |

PREPARATION EXAMPLES

Examples for the pharmaceutical preparations containing as an active ingredient the depsipeptide of the present invention will be given below.

PREPARATION EXAMPLE 1

Tablets (per tablet)

| | |
|---|---|
| Compound 20 | 20 mg |
| Magnesium silicate | 20 mg |
| Lactose | 98.5 mg |
| Hydroxypropylcellulose | 7.5 mg |
| Magnesium stearate | 1 mg |
| Hydrogenated vegetable oil | 3 mg |
| Total | 150 mg |

Compound 20, magnesium silicate and lactose were admixed and kneaded with an alcoholic solution of hydroxypropylcellulose and then granulated to an appropriate particle size, dried, and sized. Then, magnesium stearate and hydrogenated vegetable oil were added and blended to form uniform granules. The granules were then prepared to tablets by means of a rotary tableting machine, each tablet having a diameter of 7.0 mm, a weight of 150 mg and a hardness of 6 kg.

PREPARATION EXAMPLE 2

Granules

| | |
|---|---|
| Compound 20 | 10 mg |
| Magnesium oxide | 40 mg |
| Calcium hydrogenphosphate | 38 mg |
| Lactose | 10 mg |
| Hydroxypropylcellulose | 20 mg |

All the materials except for hydroxypropyl-cellulose were uniformly admixed, kneaded with an alcoholic solution of hydroxypropylcellulose and then granulated by means of an extrusion granulation machine and dried to form granules. The granules were sized so as to pass through a 12 mesh sieve and remain on a 48 mesh sieve, whereby granules were prepared.

PREPARATION EXAMPLE 3

Syrups

| | |
|---|---|
| Compound 20 | 1.000 g |
| Sucrose | 30.000 g |
| D-Sorbitol 70 w/v % | 25.000 g |
| Ethyl paraoxybenzoate | 0.030 g |
| Propyl paraoxybenzoate | 0.015 g |
| Flavoring agent | 0.200 g |
| Glycerol | 0.150 g |
| 96% Ethanol | 0.500 g |
| Purified water | q.s. |
| Total | 100 ml |

Sucrose, D-sorbitol, ethyl paraoxybenzoate, propyl paraoxybenzoate and Compound 20 were dissolved in purified water (warm water). After cooling, a solution of flavoring agent in glycerol and ethanol was added, and then purified water was added to the mixture to make up a volume to 100 ml.

PREPARATION EXAMPLE 4

Injections

| | |
|---|---|
| Sodium salt of Compound 20 | 10.0 mg |
| Sodium chloride | 81.0 mg |
| Sodium hydrogencarbonate | 8.40 mg |
| Distilled water for injection | q.s. |
| Total | 10.0 ml |

Sodium hydrogencarbonate, sodium chloride and sodium salt of Compound 20 were dissolved in distilled water to make up a total amount to 10.0 ml.

PREPARATION EXAMPLE 5

Suppositories

| | |
|---|---|
| Compound 20 | 2 g |
| Macrogol 4000 | 20 g |
| Glycerol | 78 g |
| Total | 100 g |

To a solution of Compound 20 in glycerol was added Macrogol 4000 and dissolved by warming. Then, the mixture was injected into a suppository die and solidified by cooling to prepare suppositories, each weighing 1.5 g.

What is claimed is:

1. A depsipeptide containing a non-natural amino acid(s) having the formula (1)

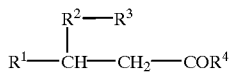
(1)

wherein
$R^1$ represents a straight or branched $C_5-C_{20}$ alkyl group or a straight or branched $C_5-C_{15}$ alkoxymethyl group,
$R^2$ represents

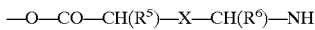

(wherein X represents $N(R^7)$—CO, $N(R^8)$—$CH_2$, $CH_2$—CO, $CH_2$—$CH_2$, CH=CH, $CH_2$—CH(OH) or CH(OH)—CH(OH), $R^5$, $R^6$, $R^7$ and $R^8$ represent a hydrogen atom or a straight or branched $C_1-C_6$ alkyl group),
$R^3$ represents

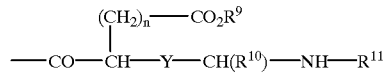

(wherein Y represents $N(R^{12})$—CO, $N(R^{13})$—$CH_2$, $CH_2$—CO, $CH_2$—$CH_2$, CH=CH, $CH_2$—CH(OH) or CH(OH)—CH(OH), n represents an integer of 1–3, $R^9$, $R^{10}$, $R^{12}$ and $R^{13}$ represent a hydrogen atom or a straight or branched $C_1-C_6$ alkyl group and $R^{11}$ represents a protecting group for an amine commonly used in peptide chemistry), $R^4$ represents a hydroxyl group, a straight or branched $C_1-C_6$ alkoxy group, a benzyloxy group, A, A—B or

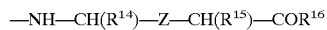

(wherein Z represents $CH_2$—$N(R^{17})$, CO—$CH_2$, CO—$N(R^{18})$, $CH_2$—$CH_2$, CH=CH, CH(OH)—$CH_2$ or CH(OH)—CH(OH), $R^{14}$ represents a hydrogen atom, a straight or branched $C_1-C_6$ alkyl group or —$(CH_2)_m$—$COR^{19}$, $R^{15}$, $R^{17}$ and $R^{18}$ represent a hydrogen atom or a straight or branched $C_1-C_6$ alkyl group, $R^{16}$ represents a hydroxyl group, a straight or branched $C_1-C_6$ alkoxy group or a benzyloxy group, $R^{19}$ represents a hydroxyl group, an amino group or a $C_1-C_6$ alkoxy group and m represents an integer of 1–3), A represents a residue of an amino acid selected from the group of alanine, valine, leucine, isoleucine, phenylalanine, tyrosine, proline, aspartic acid, asparagine, glutamic acid, glutamine, serine, lysine and β-t-butylalanine or an N-methyl derivative of said amino acid residue, B represents a residue of an amino acid selected from the group of alanine, valine, leucine, isoleucine, serine, threonine, lysine, hydroxylysine, arginine, cysteine, methionine, phenylalanine, tyrosine, tryptophan, histidine, proline, 4-hydroxyproline, aspartic acid, asparagine, glutamic acid, glutamine, piperidine-4-carboxylic acid, homoproline, octahydroindole-2-carboxylic acid, norvaline, norleucine, α-t-butylglycine, cyclohexylglycine, azetidine-2-carboxylic acid, 3-(3-pyridyl)alanine, (3-N-methyl) piperidylalanine, 3-(2-naphthyl)alanine, β-cyclohexylalanine, β-t-butylalanine, 9-anthracenylalanine, α-methylalanine and 2-aminobutanoic acid or an N-methyl derivative of said amino acid residue, when the amino acid for A or B contains a free amino group, free carboxyl group, free ω-carbamido group, free hydroxyl group, free mercapto group and/or an N-terminal amino group, said free group may be protected by a group commonly used in peptide chemistry, respectively, and when A and B are lysine, hydroxylysine, glutamic acid or aspartic acid, either α- or ω-amino or carboxyl group existing in said residue may form a peptide linkage with its adjacent amino acid;

with the proviso that compounds are excluded in which, simultaneously, X is $N(R^7)$—CO, Y is $N(R^{12})$—CO and $R^4$ is hydroxyl straight or branched alkoxy having 1–6 carbon atoms, benzyloxy, A, A—B or —NH—CH($R^{14}$)—Z—CH($R^{15}$)—$COR^{16}$ (wherein Z is CO—N ($R^{18}$));

or a pharmacologically acceptable salt thereof.

2. The depsipeptide according to claim 1 wherein X is CH=CH.

3. The depsipeptide according to claim 2 wherein X is CH=CH and Y is $N(R^{12})$—CO or $N(R^{13})$—$CH_2$.

4. The depsipeptide according to claim 3 wherein X is CH=CH, Y is $N(R^{12})$—CO or $N(R^{13})$—$CH_2$ and $R^4$ is a hydroxyl group, A, A—B or —NH—CH($R^{14}$)—Z—CH ($R^{15}$)—$COR^{16}$ (wherein Z is CH=CH).

5. The depsipeptide according to claim 3 wherein X is CH=CH, Y is $N(R^{12})$—CO and $R^4$ is a hydroxyl group, A or A—B.

6. The depsipeptide according to claim 3 wherein X is CH=CH, Y is $N(R^{13})$—$CH_2$ and $R^4$ is a hydroxyl group.

7. The depsipeptide according to claim 1 wherein X is $CH_2$—$CH_2$.

8. The depsipeptide according to claim 7 wherein X is $CH_2$—$CH_2$ and Y is $N(R^{12})$—CO.

9. The depsipeptide according to claim 7 wherein X is $CH_2$—$CH_2$, Y is $N(R^{12})$—CO and $R^4$ is A—B.

10. The depsipeptide of claim 1, wherein $R^4$ is A or A—B; or $R^4$ is —NH—$CH(R^{14}Z$—$CH(^{15})$—CO—$R^{16}$ and Z is —$CH_2$—$N(R^{17})$ or CO—$N(R^{18})$.

11. The depsipeptide of claim 1, which is represented by the formula

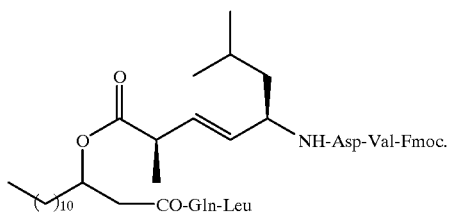

12. A pharmaceutical composition which comprises as an active ingredient a depsipeptide containing a non-natural amino acid(s) as claimed in claim 1 or a pharmacologically acceptable salt thereof.

13. A pharmaceutical composition as claimed in claim 12 for promoting the production of apolipoprotein E.

14. A pharmaceutical composition as claimed in claim 12 for treating hyperlipemia.

15. A method for treating hyperlipemia which comprises administering a therapeutically effective amount of the depsipeptide as claimed in claim 1 to a host affected with hyperlipemia.

16. A method of promoting the production of apolipoprotein E, comprising administering an effective amount of the depsipeptide of claim 1 to a host.

* * * * *